US011376182B2

(12) United States Patent
Hathorn

(10) Patent No.: US 11,376,182 B2
(45) Date of Patent: Jul. 5, 2022

(54) THERAPEUTIC UNDERGARMENTS FOR THE TREATMENT OF FUNCTIONAL GASTROINTESTINAL DISORDERS INCLUDING IRRITABLE BOWEL SYNDROME

(71) Applicant: ColoWrap, LLC., Durham, NC (US)

(72) Inventor: James Hathorn, Durham, NC (US)

(73) Assignee: ColoWrap, LLC., Durham, NC (US)

(*) Notice: Subject to any disclaimer, the term of this patent is extended or adjusted under 35 U.S.C. 154(b) by 15 days.

(21) Appl. No.: 16/413,225

(22) Filed: May 15, 2019

(65) Prior Publication Data
US 2019/0262218 A1    Aug. 29, 2019

Related U.S. Application Data

(62) Division of application No. 14/866,762, filed on Sep. 25, 2015, now Pat. No. 10,327,978.
(Continued)

(51) Int. Cl.
*A61H 7/00*   (2006.01)
*A61F 5/03*   (2006.01)
(Continued)

(52) U.S. Cl.
CPC ........... *A61H 7/001* (2013.01); *A61B 5/0533* (2013.01); *A61B 5/1107* (2013.01);
(Continued)

(58) Field of Classification Search
CPC ..... A61H 7/001; A61B 5/0533; A61B 5/1107; A61B 5/4255; A61B 5/7271; A61N 1/36014; A61N 1/36007
(Continued)

(56) References Cited

U.S. PATENT DOCUMENTS

| 5,302,171 A | 4/1994 | Pearson et al. |
| 5,885,230 A | 3/1999 | Cherry |

(Continued)

FOREIGN PATENT DOCUMENTS

| WO | 2012116407 A1 | 9/2012 | |
| WO | WO-2014039404 A1 * | 3/2014 | ........... A61B 5/0533 |

OTHER PUBLICATIONS

International Search Report and Written Opinion corresponding to International Application PCT/US2015/052400, dated Dec. 22, 2015 (9 pages).

*Primary Examiner* — Amanda K Hulbert
*Assistant Examiner* — Philip C Edwards
(74) *Attorney, Agent, or Firm* — Procopio, Cory, Hargreaves & Savitch LLP

(57) ABSTRACT

An apparatus, system, and method for analysing and/or treating symptoms of IBS. A system for treating IBS may include a processor configured to receive a first set of data from biosensors configured to measure contractions in the bowel, receive a second set of data from a galvanic skin response sensor configured to measure electrical conductance of the skin, and analyze patterns between the first and second sets of data. An apparatus may include a base material comprising a material that fits to the body of a user, an elastic portion capable of applying compression across the abdomen of a user, and a tension adjusting mechanism for adjusting the compression applied to the abdomen in order to treat the symptoms of IBS.

32 Claims, 26 Drawing Sheets

Related U.S. Application Data

(60) Provisional application No. 62/056,367, filed on Sep. 26, 2014.

(51) Int. Cl.
| | | |
|---|---|---|
| *A61N 1/36* | (2006.01) | |
| *A61B 5/0533* | (2021.01) | |
| *A61B 5/11* | (2006.01) | |
| *A61B 5/00* | (2006.01) | |
| *A61F 7/02* | (2006.01) | |
| *A61F 5/02* | (2006.01) | |
| *A61F 5/34* | (2006.01) | |
| *A61F 7/00* | (2006.01) | |

(52) U.S. Cl.
CPC .......... *A61B 5/4255* (2013.01); *A61B 5/7271* (2013.01); *A61F 5/03* (2013.01); *A61N 1/36007* (2013.01); *A61N 1/36014* (2013.01); *A61F 5/028* (2013.01); *A61F 5/34* (2013.01); *A61F 2007/0022* (2013.01); *A61F 2007/0238* (2013.01)

(58) Field of Classification Search
USPC .......................................................... 600/301
See application file for complete search history.

(56) References Cited

U.S. PATENT DOCUMENTS

| | | |
|---|---|---|
| 6,099,490 A | 8/2000 | Turtzo |
| 8,052,628 B1 | 11/2011 | Edelman et al. |
| 2002/0077688 A1 | 6/2002 | Kirkland |
| 2006/0074361 A1 | 4/2006 | Zicherman |
| 2008/0004679 A1 | 1/2008 | Naghavi et al. |
| 2008/0300649 A1* | 12/2008 | Gerber .................. A61B 7/008 607/41 |
| 2009/0077720 A1 | 3/2009 | Shinomiya |
| 2011/0125063 A1 | 5/2011 | Shalon et al. |
| 2012/0302821 A1 | 11/2012 | Burnett |
| 2013/0046150 A1* | 2/2013 | Devanaboyina ..... A61B 5/0024 600/301 |
| 2013/0178893 A1* | 7/2013 | Hathorn .................. A61F 5/37 606/201 |

\* cited by examiner

FIG. 4

| Treatment | Class | Name | Target/Mechanism of Action |
|---|---|---|---|
| Drug (OTC) | Fiber supplement | Metamucil; Citrucel | Control constipation |
| | Anti-diarrheal | Immodium | Control diarrhea |
| Drug (RX) | Antispasmodic | Levsin;Bentyl | Relieve painful bowel spasms |
| | Antidepressant | Prozac;Paxil; Tofranil | Serotonin receptors in brain, gut |
| | Antibiotic | Xifaxan | Reduce overgrowth of bacteria |
| | IBS-specific | Aloesteron; Lubiprostone | Relax/slow/lubricate colon |
| Dietary | Gluten-free; dairy-free; etc. | | Limit food causing bloating, gas, cramps |
| | Probiotics (Activia with Cultures) | | Promote growth of healthy gut microflora |
| Psychological | Cognitive-Behavioral Therapy | | Confront irrational anxious thoughts |

FIG. 7
The pressure distends the colon, thereby increasing the circumference of the colonic lumen.
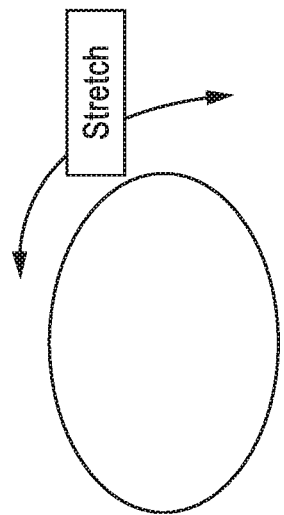
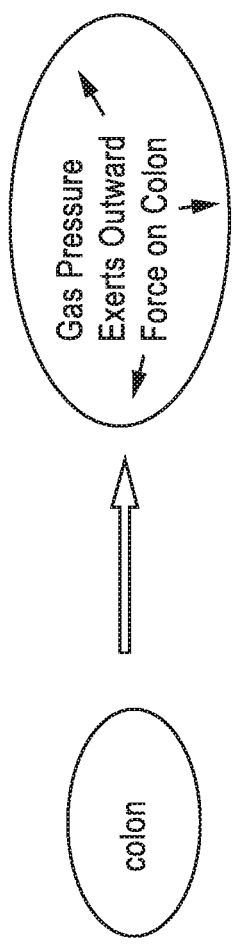
This increase in circumference triggers afferent signal pathways on stretch receptors within the circular muscle layer of the colon wall.

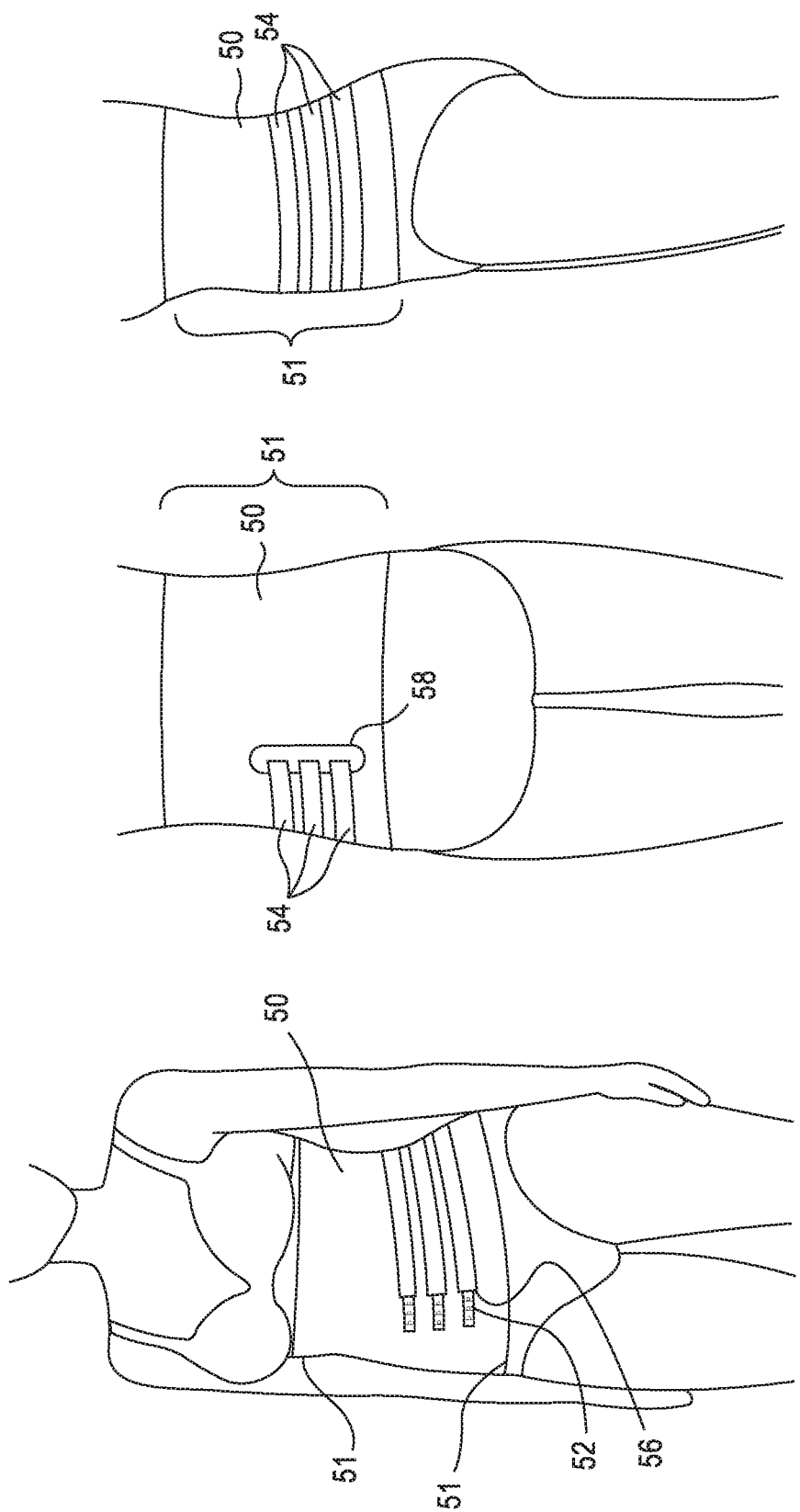

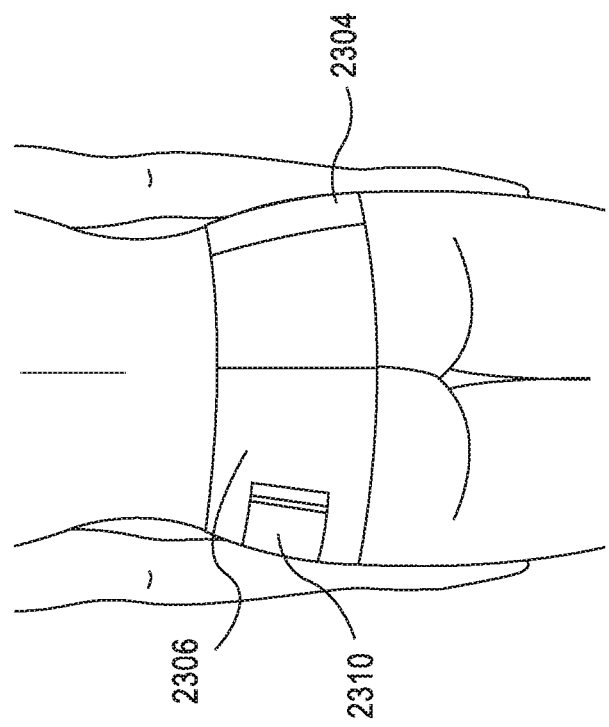
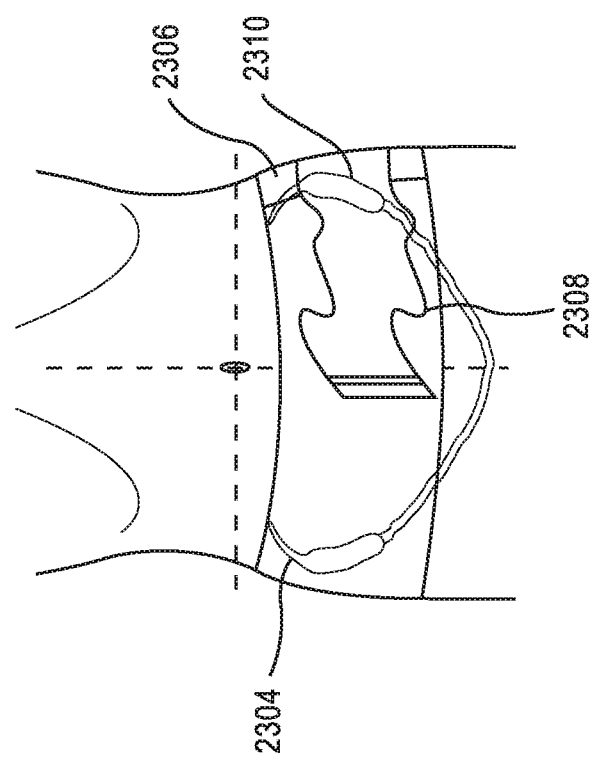
FIG. 23A
FIG. 23B

THERAPEUTIC UNDERGARMENTS FOR THE TREATMENT OF FUNCTIONAL GASTROINTESTINAL DISORDERS INCLUDING IRRITABLE BOWEL SYNDROME

CROSS-REFERENCE TO RELATED APPLICATION

This application is a divisional of U.S. application Ser. No. 14/866,762, entitled "THERAPEUTIC UNDERGARMENTS FOR THE TREATMENT OF FUNCTIONAL GASTROINTESTINAL DISORDERS INCLUDING IRRITABLE BOWEL SYNDROME" and filed on Sep. 25, 2015, which claims the benefit of U.S. application Ser. No. 62/056,367, entitled "THERAPEUTIC UNDERGARMENTS FOR THE TREATMENT OF FUNCTIONAL GASTROINTESTINAL DISORDERS INCLUDING IRRITABLE BOWEL SYNDROME" and filed on Sep. 26, 2014, the entire contents of both of which are expressly incorporated by reference herein in their entirety.

BACKGROUND

Field

Aspects of the present disclosure relate to a method and apparatus for treating functional gastrointestinal disorders including irritable bowel syndrome.

Description of the Related Art

Functional gastrointestinal disorders (FGIDs) are disorders that are characterized by persistent and recurring gastrointestinal (GI) symptoms. These occur as a result of abnormal functioning of the GI tract. They are not caused by structural (tumors or masses) or biochemical abnormalities. The most prevalent FGID is Irritable Bowel Syndrome (IBS)—abdominal pain associated with altered bowel habits of diarrhea, constipation or both. Bloating and abdominal distention are also frequently reported by patients with IBS.

IBS affects up to 15% of the US adult population. 50-80% of people with IBS symptoms do not consult a physician, although they may take over-the-counter medications and report significantly more job absenteeism and disability than people without these symptoms. It has been reported that IBS is the second leading cause, after the common cold, for missing work or school.

SUMMARY

Aspects presented herein include a method and apparatus for treating Functional Gastrointestinal Disorders, including Irritable Bowel Syndrome. Aspects can be deployed, activated, engaged, and/or adjusted in real-time to help patients manage acute symptoms of IBS and provide patients with control, both real and perceived, over the symptoms of IBS and its impact on their lives.

Aspects of the disclosure include an apparatus for treating symptoms of IBS. The apparatus includes a base material comprising a material that fits to the body of a user, an elastic portion capable of applying compression across the abdomen of a user, and a tension adjusting mechanism for adjusting the compression applied to the abdomen in order to treat the symptoms of IBS.

Aspects also include a system for treating IBS, the system having a processor configured to receive a first set of data from biosensors configured to measure contractions in the bowel, receive a second set of data from a galvanic skin response sensor configured to measure electrical conductance of the skin; and, analyze patterns between the first and second sets of data.

Aspects further include a method of treating IBS symptoms comprising applying a base material garment comprising a material that fits to the body of a user, tensioning an elastic portion capable of applying compression across the abdomen of a user, and adjusting the compression applied to the abdomen in order to treat the symptoms of IBS.

Additional advantages and novel features of aspects of the present invention will be set forth in part in the description that follows, and in part will become more apparent to those skilled in the art upon examination of the following or upon learning by practice thereof.

BRIEF DESCRIPTION OF THE DRAWINGS

FIG. 4 is a table listing common IBS treatments by type.

FIG. 7 is a schematic view of the manner by which gas pressure distends the colon outward and activates stretch receptors.

FIGS. 9A-9C provide perspective views from the front, back, and side of a female patient wearing an example apparatus in accordance with aspects of the present invention, worn about the torso, from just below the bust line down to the pubic line.

FIGS. 23A and 23B provide perspective views from the front and back of a female patient, wearing an example apparatus in accordance with aspects of the present invention comprising an abdominal band.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

While the etiology of IBS remains unclear, at least three primary mechanisms may produce symptoms of IBS: Dysmotility, Visceral Hypersensitivity, and Brain-Gut Dysfunction.

Motility involves the muscular activity of the GI tract, which is essentially a hollow, muscular tube. Normal motility includes an orderly sequence of muscular contractions from top to bottom. In IBS, motility is abnormal. There can be muscular spasms that cause pain and the contractions can be very rapid, or very slow or disorganized, leading to diarrhea and constipation, respectively. This is known as dysmotility.

Sensation involves how the nerves of the GI tract respond to stimuli (e.g., food, digesting a meal, intestinal gas). In IBS, the nerves are sometimes so sensitive that even normal contractions can bring on pain or discomfort. This is known as visceral hypersensitivity.

Brain-gut dysfunction involves the disharmony in the way that the brain and GI system communicate. With IBS, the regulatory conduit between brain and gut function may be impaired in a way where IBS symptoms beget anxiety which beget additional symptoms, and so on.

Figure 1:
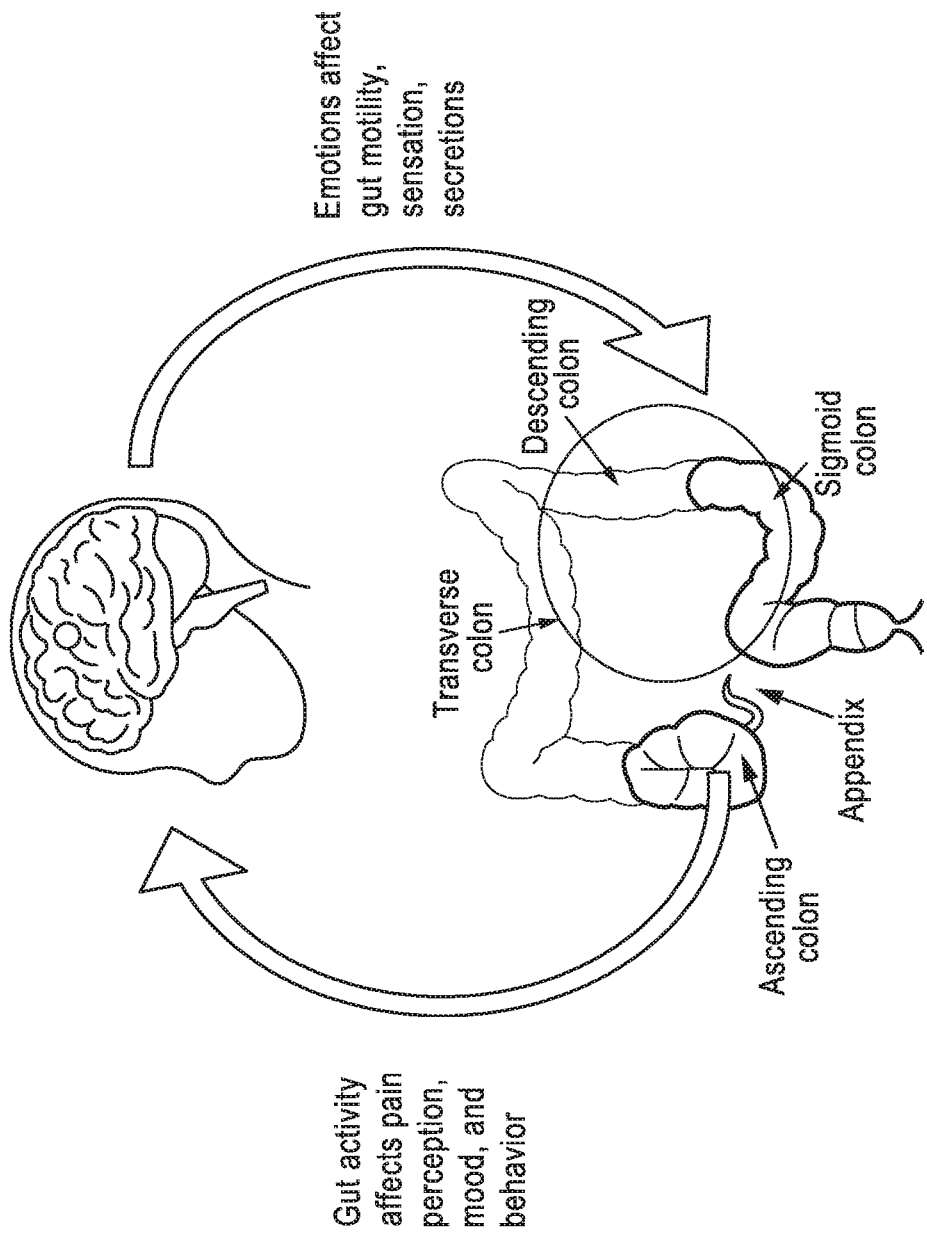
FIG. 1 is a schematic view of the function of the Brain-Gut Axis.

The communication between the brain and the gut via the nervous system is known as the brain-gut axis. The relationship is bi-directional in nature, as depicted in FIG. 1. This means that activities in the gut can affect mood, perception, and behavior, and reciprocally that emotions can affect gut activity. An example of the brain-gut axis is the statement, "I have butterflies in my stomach," from a person anticipating a dramatic or stressful event.

Given the involvement of the brain in IBS, researchers have attempted to characterize the disorder with explanatory models that incorporate components derived from psychological theories. Particularly relevant to IBS is the cognitive behavioral approach. Similar to the brain-gut axis concept, cognitive behavioral theory stipulates that the relationship between thoughts, feelings, and behaviors (or physiological outcomes) is bi-directional: certain thoughts provoke certain emotions that have a tendency to precipitate certain behaviors, and vice versa. The nature of this relationship serves as the basis for the cognitive behavioral model for IBS as well as for cognitive behavioral therapy (CBT).

The goal of cognitive behavioral therapy is to help patients change undesirable emotions, behaviors, or physiological responses by examining the patient's underlying thoughts, mental processes, and interpretations of events. Cognitive psychology holds that the brain makes numerous assumptions (also known as heuristics) that help filter stimuli and allow decisions to be made quickly and efficiently. Individuals are generally unaware of these assumptions and this is typically an asset. However, when a maladaptive or irrational assumption becomes the basis for mental assessment or interpretation, undesired feelings and behaviors are often the result. Yet despite negative consequences, individuals struggle to identify the disordered thinking that leads to the undesired outcomes.

Behavioral psychology focuses on the underlying processes, emotions, and motivations that influence behavior. The behavioral psychology contribution most relevant to CBT is the concept of reinforcement. Reinforcement is anything that can make a person more or less likely to repeat a certain behavior. Punishment is also a type of reinforcement but is not discussed as it is less relevant. Reinforcement can be positive or negative, as well as internal or external. The table below provides an example of common types of reinforcement:

|  | Internal (Intrinsic) | External (Extrinsic) |
|---|---|---|
| Positive (Something is added) | Artist completes a masterpiece work; Provokes feelings of satisfaction, boosts self-esteem; Artists will continuing painting with passion | Child gets straight A's in school; Parents give child $10 for each A; Child gets straight A's again. |
| Negative (Something is taken away) | Person with OCD has (irrational) fear of contamination, relieves anxiety by washing hands and avoiding shaking with others; behaviors will be constant, ritualistic over time | POW won't reveal key information; Painful electric charge is applied to body by captors; POW reveals key information to avoid reapplication of painful charge |

Cognitive behavioral therapy incorporates the concept of reinforcement to help explain the chronic nature of many psychological disorders or physiological disorders with a psychological component. A straightforward example of the role of reinforcement is addiction. Consider a man that is experiencing heightened anxiety due to recent job loss. Despite an upcoming interview with a new firm, he feels that he's "never measured up and can't understand why the firm would want him."

This mental state is unpleasant. One evening after several glasses of wine he realizes he feels more relaxed and less anxious. As a result, the next evening when he feels anxious, he repeats the behavior (drinking alcohol) in order to achieve the desired effect. He then begins drinking during the day to relieve his anxiety over unemployment. When he finally has his job interview, he is very anxious and he drinks prior to the interview to relieve this anxiety. The employer notices that he is intoxicated and does not offer him the job. Losing the job opportunity provokes greater anxiety for the man, which leads him to drink more frequently, creating additional negative consequences. This example demonstrates how an irrational assumption ("They'd never hire me") can lead to a mental state (anxiety) that is resolved by an undesirable behavior, the impact of which leads an outcome that validates the original, maladaptive assumption (e.g. he isn't hired for the job, provoking greater anxiety and more drinking). This is known as a positive or self-perpetuating feedback loop: disordered thoughts, emotions, and behaviors reinforce themselves in a continual process.

Figure 2:
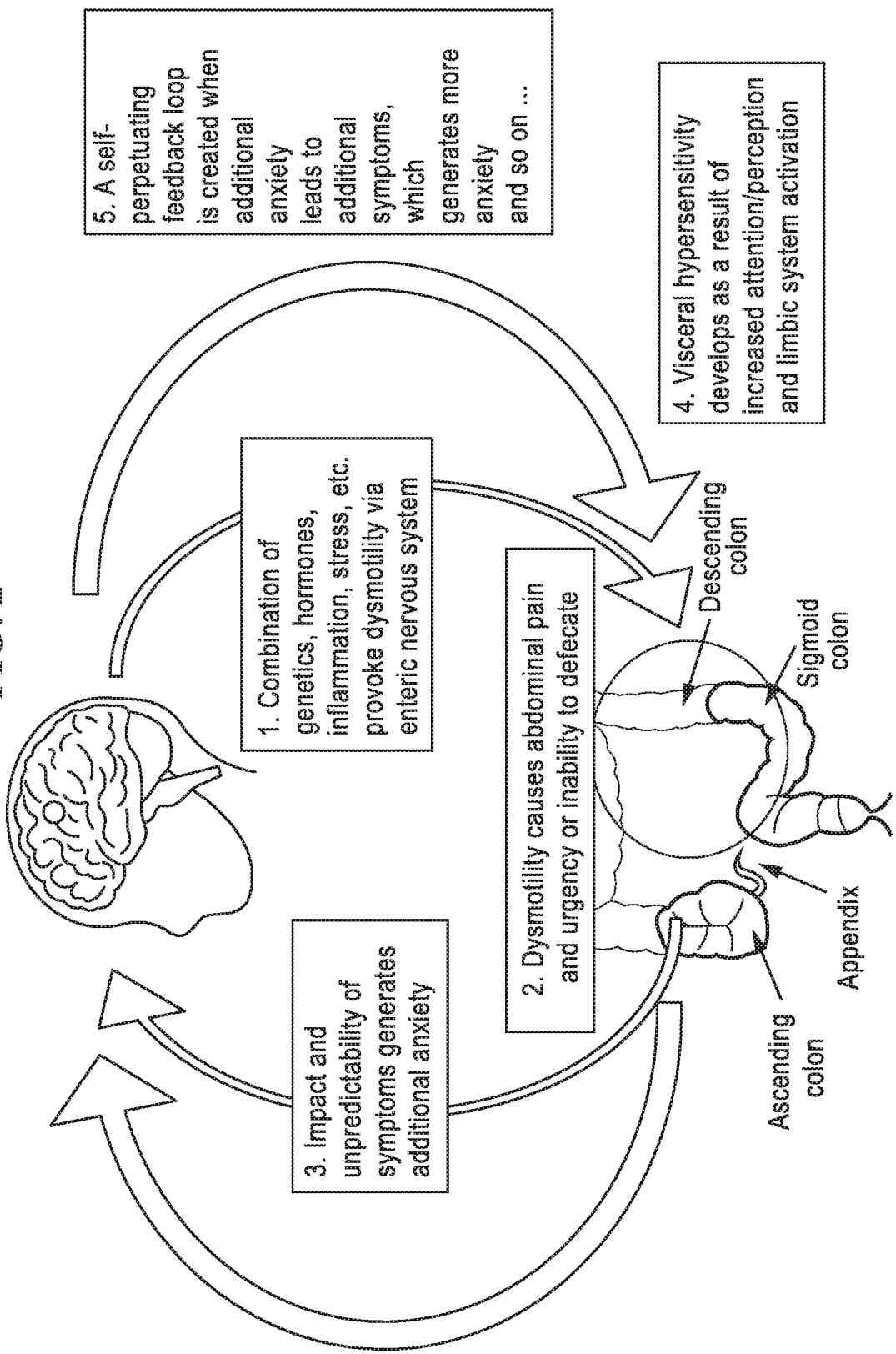
FIG. 2 is a schematic view of how IBS can become a chronic, self-perpetuating syndrome.

The concept of the self-perpetuating feedback loop is very applicable to IBS, and is illustrated in FIG. 2. The cognitive behavior model of IBS proposes that symptoms (e.g. abdominal pain, dysmotility, bloating) originate due to a combination of factors including genetic predisposition, infection, inflammation, hormonal changes, altered gut microbiota, illness, and stressful life events. As the symptoms of IBS are unpleasant and disruptive, patients become fearful and anxious that the symptoms will reoccur. This anxious state leads to dysmotility via the brain-gut axis while promoting increased attention to and perception of visceral sensation, resulting in hypersensitivity. Dysmotility and hypersensitivity lead to additional IBS symptoms and life disruption, which generates additional anxiety, and thus the cycle perpetuates.

Figure 3:
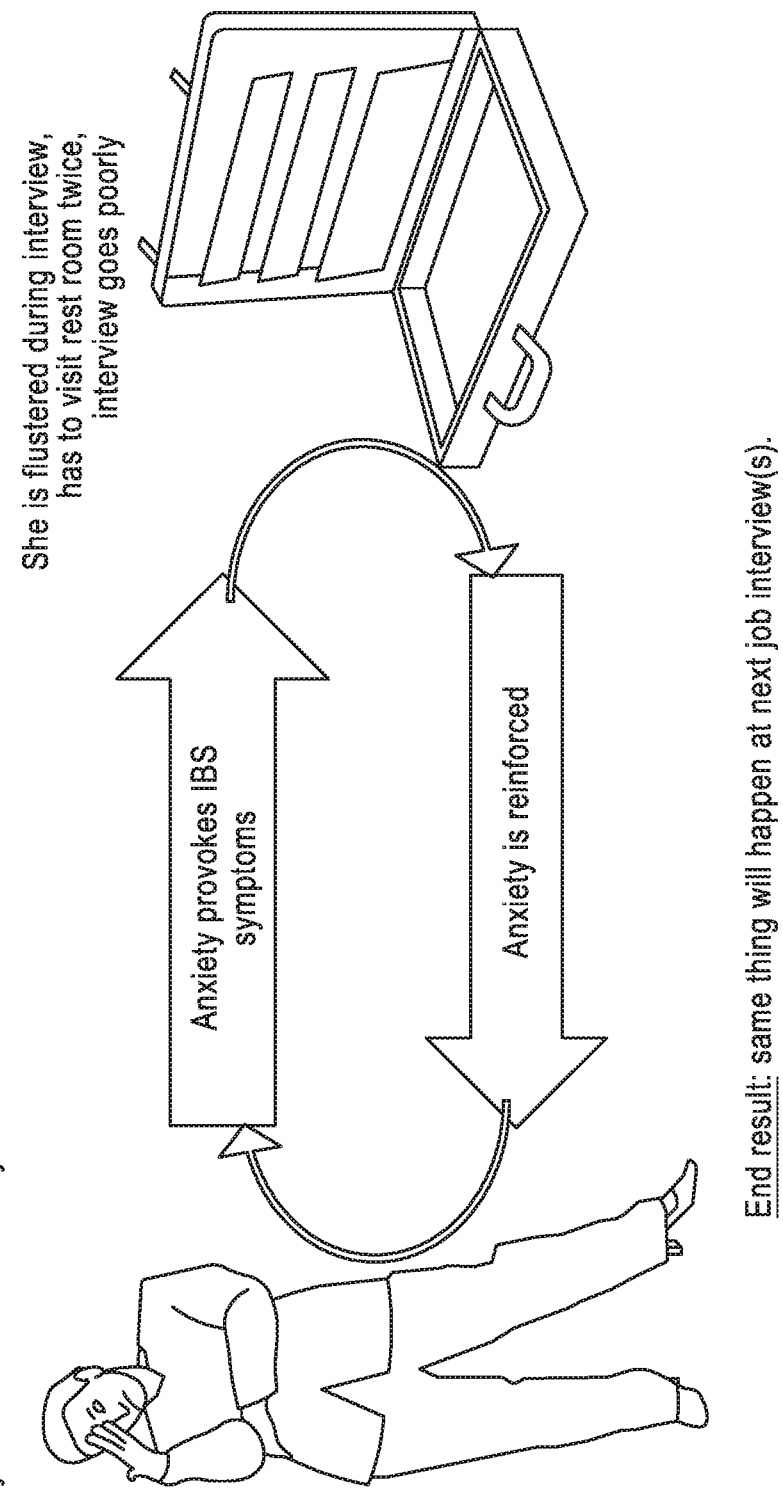
FIG. 3 is a conceptual example of the manner by which IBS can become a chronic, self-perpetuating syndrome.
Figure 5:
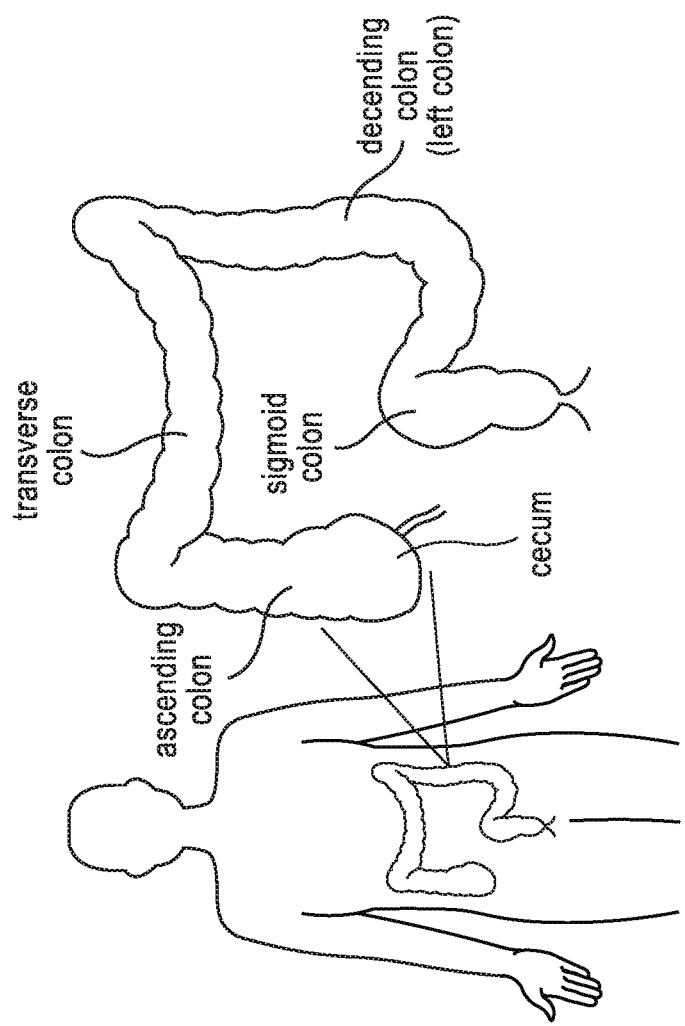
FIG. 5 is a schematic view of the colon, set inside the outline of a male human body on the left, and magnified on the right with various parts of the colon identified.

A conceptual example of how IBS is perpetuated, resulting in impaired quality of life, is provided in FIG. 3. As illustrated in FIG. 3, an individual is anxious about experiencing IBS symptoms during a job interview. The job applicant's anxiety provokes IBS symptoms, causing her to become flustered during the interview. The IBS symptoms also cause her to visit the rest room twice. The interview goes poorly, which further reinforces her anxiety regarding her IBS symptoms. This reinforcement heightens her anxiety at the next interview which will result in the same IBS symptoms.

Despite the significant social and economic impact of IBS and the variety of available treatments, there is no 'silver-bullet' to treat the disorder. A list of current treatments is displayed in FIG. 4. These treatments are similar in that they are all only marginally effective. In addition, certain treatments such as prescription medications are very expensive.

That currently available treatments for IBS are consistently effective, yet only marginally so, is due to the fact that they are primarily treating the physiological symptoms of the disorder, while leaving the psychological component relatively unaddressed. To better understand why existing treatments are only marginally effective, it is helpful to introduce a third psychological concept: Locus of control.

Locus of control refers to the extent to which individuals believe they can control events that affect them. This belief is significantly influenced by an individual's previous experiences and they way he or she interpreted them. Individuals with a strong, internal locus of control believe that they can affect outcomes with their behavior, while those with a weak, external locus generally attribute outcomes to factors over which they have no control or influence. Beliefs associated with a weak locus of control (e.g. "It doesn't matter what I do, the outcome won't change" and "Why should I even try?") are associated with anxiety, depression, and other psychological disorders; conversely, even small instances of control (e.g. a child deciding how to organize his or her bedroom) tend to promote improved self-esteem and mental wellbeing.

Patients generally have a very weak locus of control with respect to IBS due to the unpredictability of the symptoms and their inability to prevent or inhibit them. In fact, often IBS patients feel that the symptoms occur "always at the worst possible time, as if someone is playing a mean joke on me", in their eyes maximizing the negative impact on their life. What many patients fail to realize is that they are also more anxious during periods which an IBS attack would be "devastating", simply due to the enhanced importance of the situation, such as a job interview.

Returning to the currently available treatments for IBS, each acts in an indirect, non-acute manner to reduce symptoms, despite the fact that the patient with IBS experiences the symptoms in a very acute, direct way. As a result, none of the current treatments effectively improve the patient's sense of control over the symptoms. The need for IBS treatments that take into account patients' sense of control is exemplified by the fact that in IBS drug studies dosing frequency (when cumulative dosing amount is held constant) shows a strong positive correlation with efficacy in both drug and placebo study groups. The more frequent the dosing, the greater the efficacy, implying that the patients who received the most benefit are those given the ability to take specific action (e.g. take a dose) that they perceive will reduce current IBS symptoms or reduce the likelihood of an acute occurrence of IBS symptoms.

Neglecting the patient need for acute control and symptom management inhibits currents treatments from being maximally effective. Although some efficacy in symptom reduction is achieved, the treatment behavior (e.g. taking a pill in the morning, avoiding dairy products) is too far removed from the patient's acute experience of symptoms (or lack thereof) to create and reinforce a strong positive association in the patient's mind between their action and symptom relief or non-occurrence. (Consider the results had Pavlov rung his bell 6 hours before feeding his dogs versus immediately prior to the meal.) As a result, despite some efficacy in reducing symptoms, current treatments fail to effectively interrupt the IBS feedback loop thus and remain only marginally effective.

Accordingly, there is a great need for IBS treatment modalities that not only target and reduce symptoms, but also provide patients with a sense of control over the syndrome and its impact on their lives. The latter can be most effectively achieved with treatments that can be acutely deployed and augmented by the patient in response to symptoms or to the (patient's) expectation of symptoms in the near-term Aspects presented herein include a method and apparatus for treating Functional Gastrointestinal Disorders, including Irritable Bowel Syndrome. Aspects can be deployed, activated, engaged, and/or adjusted in real-time to help patients manage acute symptoms of IBS and provide patients with control, both real and perceived, over the symptoms of IBS and its impact on their lives.

An abdominal wrap, as presented herein, generates broad, uniform lower abdominal pressure and delivers additional, focused pressure to the sigmoid and descending colon, which helps to reduce IBS symptoms. Research yielded the identification of several mechanisms of action that we hypothesize are responsible for this unexpected, previously unknown efficacy. These mechanisms are described in the table below.

| Intervention | Application Site | Target Symptom/Mechanism of Action |
|---|---|---|
| Compression | Sigmoid Colon; Sigmoid/Descending Colon | Dysmotility; compression reduces and prevents spasms in sigmoid/descending colon and relax the muscles. This returns contractions to normal. |
| Compression | Sigmoid/Descending colon; Lower abdomen generally | Hypersensitivity/pain; Gate control theory: transcutaneous pressure applied to anatomical site(s) from which pain signals originate blocks pain signals from reaching brain. |
| Compression | Sigmoid/Descending colon | Distention/Bloating: Externally applied compression prevents excessive expansion of colon lumen due to accumulation of gas. |
| Artificial abdominal wall resistance | Lower abdomen generally Sigmoid/Descending colon; | Distention/Bloating: Artificial abdominal wall resistance counteracts abnormal, paradoxical abdominal wall musculature response to intestinal gas and pressure that occurs in patients with IBS. |
| Acutely deployed, patient-modulated treatment | Sigmoid/Descending colon; Lower abdomen generally | Brain-Gut Axis Dysfunction: Provides patients with control (real and perceived) over symptoms and symptom management. Inhibits IBS feedback loop far more effectively than current treatments. |

Additional mechanisms that may also be useful in treating IBS include the following.

| | | |
|---|---|---|
| Hot Compression | Sigmoid/Descending colon | Dysmotility: heat to help relieve spasms and relax muscle. |
| Hot/Cold Compression | Sigmoid/Descending colon; Lower abdomen generally | Hypersensitivity/pain: Hot and cold compress to block pain signals when applied to site of signal generation. For example, a study at the University College of London used DNA technology to monitor heat and pain receptors within cells. Temperatures over 104 F. switched on internal heat receptors (TRPV1) which block the effect of chemical messengers that cause pain on the pain receptor (P2X3). |
| Transcutaneous Electrical Nerve Stimulation (TENS) | Sigmoid Colon; Sigmoid/Descending Colon; Lumbar | Hypersensitivity/pain; Gate control theory, electrical signals generated by TENS applicator inhibit pain signal generation when applied to site of pain. Also possible to inhibit pain signals through application of TENS to site at which nerves innervating pain site connect to spinal chord. |
| Reciprocal Inhibition | Lumbar, Abdominal Wall | Distention/Bloating: Reciprocal inhibition is tendency for muscles on one side of joint/axis to relax in response to contraction of muscles on other side. Mechanisms that relax muscles in lower back/lumbar region can promote contraction of abdominal wall to counteract abnormal relaxation in patients with IBS. |
| Biofeedback | Abdominal Wall | Distention/Bloating: Wearable mechanism that detects and measures contraction and relaxation of abdominal wall and provides feedback to the wearer when unconscious relaxation of the abdominal wall is occurring, so that the user can recognize this and consciously contract the abdominal wall in response. |
| Biofeedback | Sigmoid/Descending colon; Lower abdomen; Skin generally | Brain-Gut Axis Dysfunction; Biosensors capture and store physiological data (e.g. heart rate, muscle contractions, perspiration, bowel movements, etc..). When stored/captured alongside concurrent thoughts/feelings/behaviors, can provide basis for pattern recognition and therapy. |

The various aspects disclosed herein incorporate one or more of these treatment mechanisms into forms and designs that are easily integrated into patients' lives.

Figure 6:
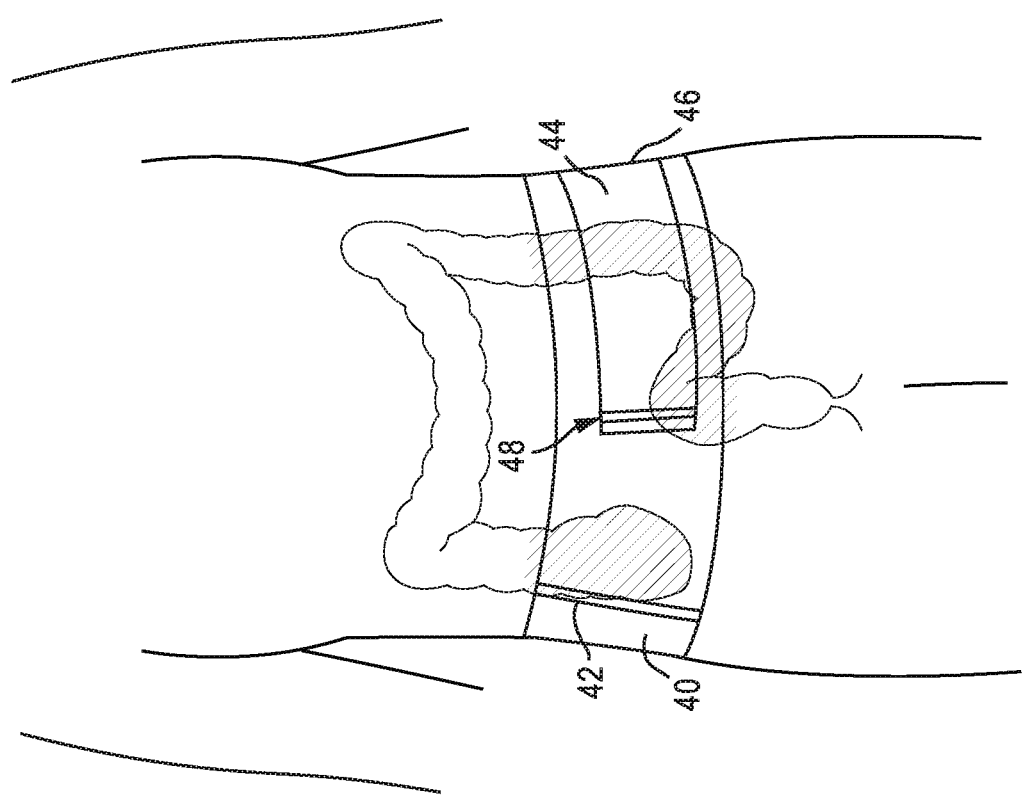
FIG. 6 is a semi-perspective view of one example apparatus, in accordance with aspects of the present invention; the parts of the colon that are compressed by this example being highlighted.

One example, in according with aspects of the present invention, depicted in FIG. 6, includes an elastic or semi-elastic band 40 that is wrapped externally around the patient's lower abdomen, with one side of the band being fastened securely to the other side of the band with a closing mechanism 42. On the exterior of the band 40, there may be an elastic or semi-elastic secondary band 44 that may be attached so that when its sewn edge 46 is properly positioned behind the patient's left hip, the secondary band 44 may be stretched horizontally across the left lower abdomen (sigmoid and descending colon area) and secured to the exterior of the primary band 40 with a closing mechanism 48. This example includes aspects that apply compression to the colon as indicated by the highlighted regions of the colon depicted in FIG. 6. The treatment effect of this embodiment (compression) may be adjusted by the patient using the closing mechanism 48 on the secondary band 44.

General lower abdominal pressure is generated along with additional, targeted pressure to the sigmoid and descending colon. The sigmoid and descending colon regions (collectively known as the left colon) are generally the most problematic anatomical sites for IBS patients. The sigmoid colon is the part of the large intestine known to have the most dense, and thus the strongest, muscular fibers. Stool is desiccated and packaged into a solid form by the time it reaches this area. As a result, stronger muscular contractions are required to push the stool down into the rectum and then to evacuate it. This area is not only the most muscular portion of the colon but is often the most redundant, demonstrating loops of elongated bowel that trap gas and portions of stool.

Aspects presented herein reduce symptoms for IBS patient by targeting two different mechanisms, each addressing a hallmark feature of the syndrome (dysmotility and visceral hypersensitivity, respectively). Dysmotility is typically associated with painful cramps and diarrhea, constipation, or both, due to spasms in the patient's left colon. The invention targets this area with focused compression. When the device is applied, the frequency and intensity of the spasms are reduced, and the colon relaxes into a more normal contraction pattern.

The other IBS hallmark feature the invention addresses is visceral hypersensitivity. This is the tendency for patients with IBS to 'over feel' digestive activities in their bowels relative to non-IBS patient counterparts. In studies, IBS patients report pain (due to gas, bloating, distention, spasms, pressure, etc.) when healthy patients exposed to the same stimuli (e.g. same volume of gas in sigmoid colon) do not. Hypersensitivity is caused by dysfunction in the way the brain and gut communicate via the nervous system. Although the specific mechanism of dysfunction remains unclear, certain nerve pathways that connect the gut to areas in the brain associated with pain may become overactive in patients with IBS, while likewise, pathways that dampen pain sensitivity may become inhibited.

The invention reduces visceral hypersensitivity by providing a stimuli that 'closes the gate' and blocks pain signals from reaching the brain. The phrase 'closing the gate' refers to the Gate Control Theory of Pain, first proposed in 1965 by Ronald Melzack and Patrick Wall. Gate Control Theory states that the activation of nerves which do not transmit pain can interfere with signals from pain fibers, thereby inhibiting pain. As a result of the compressive force generated across the sigmoid and descending colon particularly, and the lower abdomen generally, the invention stimulates non-pain nerve pathways that help block the overactive pain pathways present in IBS patients.

The invention also provides relief from bloating and distention, both very common symptoms of IBS. The device helps in three ways: 1) by limiting the circumference of the colon, particularly in the descending and sigmoid areas; 2) by providing artificial abdominal wall resistance, and; 3) by provoking contraction of the abdominal muscles and diaphragm.

Figure 8:
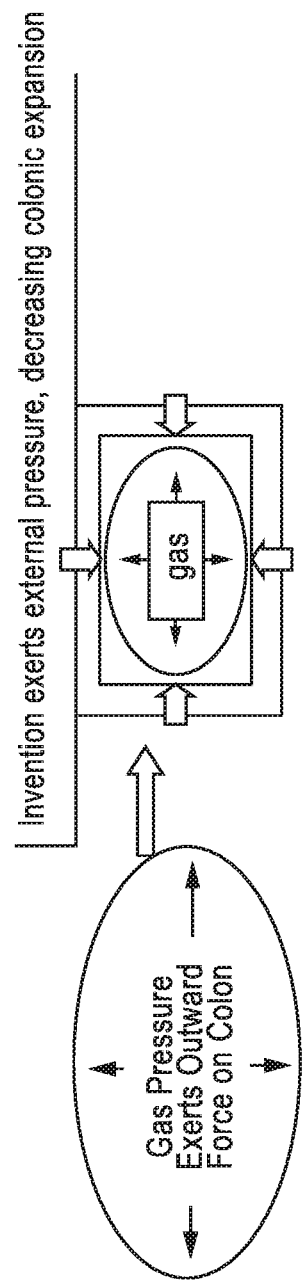
FIG. 8 is a schematic view of how aspects of the invention exert external compression and counteracts colonic expansion.

The circumference of the colon can grown in response to gas pressure. Gas pressure inside the colon exerts outward force on the colon wall, thereby increasing the circumference of the colonic lumen. (See FIG. 7). The increase in circumference triggers afferent signal pathways on stretch receptors within the circular muscle layer of the colon wall. The afferent receptors then send a signal of pain to the brain (See FIG. 7). When the compression is applied, the compression translates external force into the abdominal cavity and onto the walls of the colon. This external pressure helps counter the internal pressure generated by colonic gas, preventing a large increase in the circumference and stretch of the colon wall (See FIG. 8).

Aspects presented herein also provide artificial abdominal wall resistance. This is important due to the fact that the abdominal muscles and diaphragm of patients with IBS tend to have an abnormal post-prandial response to a meal and well as general intestinal gas and pressure. In healthy patients, the abdominal wall and diaphragm generally contracts and tightens following a meal or in response to intestinal gas and pressure. The exact opposite is true, however, in patients with bloating and distention. In response to food intake, gas, and pressure, the abdominal wall and diaphragm of patients that experience bloating and distention tend to paradoxically relax rather than contract, allowing the stomach and abdomen to shift downward and outward. By providing both general abdominal compression, as well as focused compression to the sigmoid area, the invention compensates for IBS patients' inappropriate relaxation of the abdominal wall. This means that bloating, gas, and distention are reduced. Other aspects of the invention may reduce bloating and distention by provoking contraction of the abdominal muscles and diaphragm, or by reminding the patient to actively contract these muscles, in order to counteract abnormal relaxation. Aspects that may be incorporated to provoke muscle contraction include transducers that apply transcutaneous electro-stimulation to the affected region (direct stimulation) as well as aspects that provoke contraction using one or more of the human bodies known reflex responses (indirect stimulation) such as reciprocal inhibition and the superficial abdominal reflex. The superficial abdominal reflex refers to the tendency for the abdominal wall to contract in response to gentle stimuli (such as a light stroking by a finger) applied upon the skin surface of the abdomen.

Another mechanism that contributes to the invention's effectiveness in treating IBS is the fact it can be deployed or engaged rapidly by the patient to address acute symptoms, and that its primary treatment mechanisms are easily adjustable by the patient. As previously discussed, providing IBS patients with a greater sense of control over their treatment and symptoms aligns well with the suspected psycho-pathophysiology of the disorder. That is, by allowing them to feel in control of managing 'treatment level' and symptom reduction, the probability of the patient having successful experiences that he or she attributes to his or her own action will increase. This will create meaningful reductions in the patient's anxiety over time as his or her sense of control and confidence is repeatedly reinforced.

Aspects presented herein may include incorporating treatment mechanisms into undergarments that patients can wear under their normal clothes during the day. The undergarments may be sewn in various shapes and sizes and for male and female physiques. In general, the apparatus may be sewn with fabrics and in such a way that it adheres relatively closely or tightly to the body of the wearer. This can be important because it allows the garment to be relatively tight fitting, and adhere to the body of the wearer, to enable the therapeutic features of the garment to be optimally deployed. The garment may be predominantly composed of one or more fabrics such as nylon, neoprene, cotton, spandex, polyester, synthetic fiber fabric, or any other fabric or material known for use in athletic, high-performance, and specialty purpose clothing. The garment may comprise, e.g., a fabric, composite, or material that is capable of being worn under clothing. The garment may cover at least the sigmoid colon region of the torso. The garment may incorporate one or more features that affect the sigmoid and descending colon and/or the general abdominal and lumbar region for the purpose of reducing symptoms of FGIDs including irritable bowel syndrome. The mechanism of action of these features may include providing support and compression, heat or cold therapy, and stimuli, including electrical, magnetic, sonic, or any other type of stimuli know for use to inhibit or excite certain sensory pathways; also, monitoring and transmitting bio-signals, providing artificial abdominal wall resistance, responding automatically to bio-signals, providing biofeedback to the patient, providing mechanisms that allow the patient to adjust of treatment effect, providing pressure or trigger point therapy, providing pressure or trigger point therapy to induce relaxation or contraction of abdominal, pelvic, and lower back (lumbar) musculature.

The garments may designed to be worn as undergarments for symptom relief during the day. Unless otherwise noted, the base or primary material for the example undergarments will be denoted with 50 in each illustration. The base material 50 for each undergarment may be predominantly composed of one or more fabrics such as nylon, neoprene, cotton, spandex, polyester, synthetic fiber fabric, or any other fabric or material known for use in athletic, high-performance, and specialty purpose clothing. In this regard, the base material of the garment, or at least a significant portion of the garment, may be composed of a fabric or composite that has elastic or semi-elastic properties similar to garments generally known as 'Shapewear', or if relatively inelastic, be composed of a material that closely fits the intended wearer. The garment may be composed predominantly of a fabric, composite, or material that is capable of being worn comfortably under primary clothing.

One example comprises a shape-fitting undergarment for female patients that covers the torso from the pubic line to just below the bust line. This example is illustrated in FIGS. 9A, 9B, and 9C. Sewn horizontally across the lower front portion of the undergarment 51 are several strips of hook-compatible loop material 52. Additional elastic or semi-elastic strips 54 may be sewn to the undergarment so that they extend horizontally from just behind the patients left hip around the left hip and across the left lower abdomen from left to right. The strips 54 can then be stretched from left to right across the lower abdomen and fastened to the loop strips 52 using a hook closing mechanism 56 attached to the elastic strips 54. In this example, it may be important that some vertical space, even if minimal, be left between the horizontally sewn loop strips 52 and elastic strips 54. Providing space will allow the apparatus to generate compression, but will prevent the tendency for the elastic straps to roll when the patient bends at the waist. Also, there may be a reinforcement 58 sewn into the back side of the garment, near where the elastic strips 56 are sewn to the primary material 50. This reinforcement 58 may help prevent the elastic strips 56 from pulling the base material 50 out of place when the strips 56 are stretched and fastened.

Figure 10B:
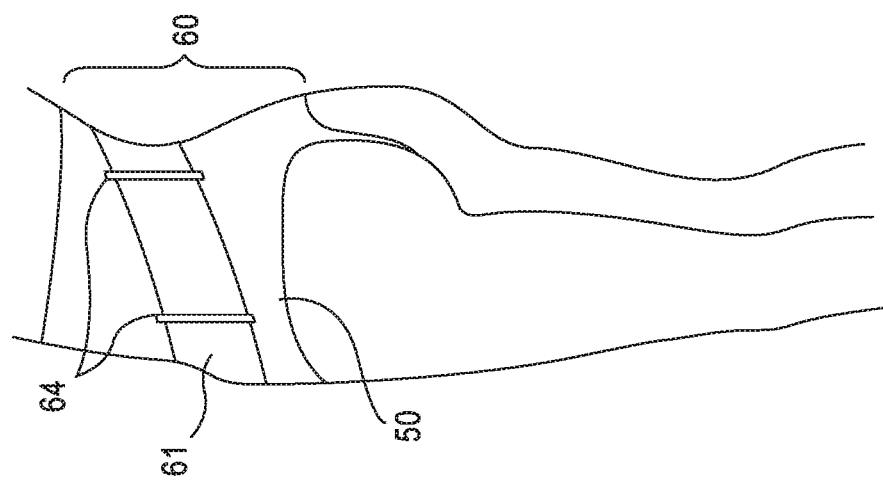
FIGS. 10A and 10B provide perspective views from the front and angled back of a female patient wearing an example apparatus in accordance with aspects of the present invention comprising a thong bottom with an undergarment extension that covers the torso up to the rib line.
Figure 10A:
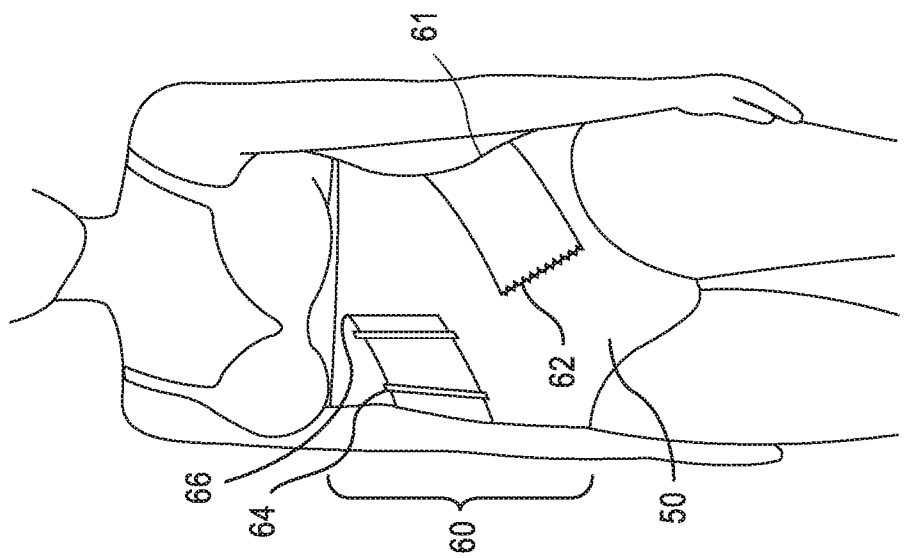

In an alternative example 60 for female patients, illustrated in FIGS. 10A and 10B, base material 50 comprises thong underwear that extends up across the torso to just below the bust line. There is an elastic or semi-elastic strap 61 that is sewn at an angle on its bottom end across the left lower abdomen, below the umbilicus. The strap 61 the extends out over the left hip and wraps around the patient's back from left to right, finally re-emerging on the patient's front right side, just below the diaphragm. In being wound around the patient's body, the strap 61 is passed through several simple loops 64 sewn to the base material 50 that help keep the strap 61 in place. The strap 61 is fastened to the top portion of the undergarment using a closing mechanism 66. This example may be desirable because compression of the sigmoid and descending colon is achieved without having straps or compression materials wrapped across the lower abdomen which is undesirable for certain patients. Additional aspects may include a second strap that begins on the right side of the abdomen, opposite from the strap 60, and circumvents the patients body in the opposite direction.

Figure 11B:
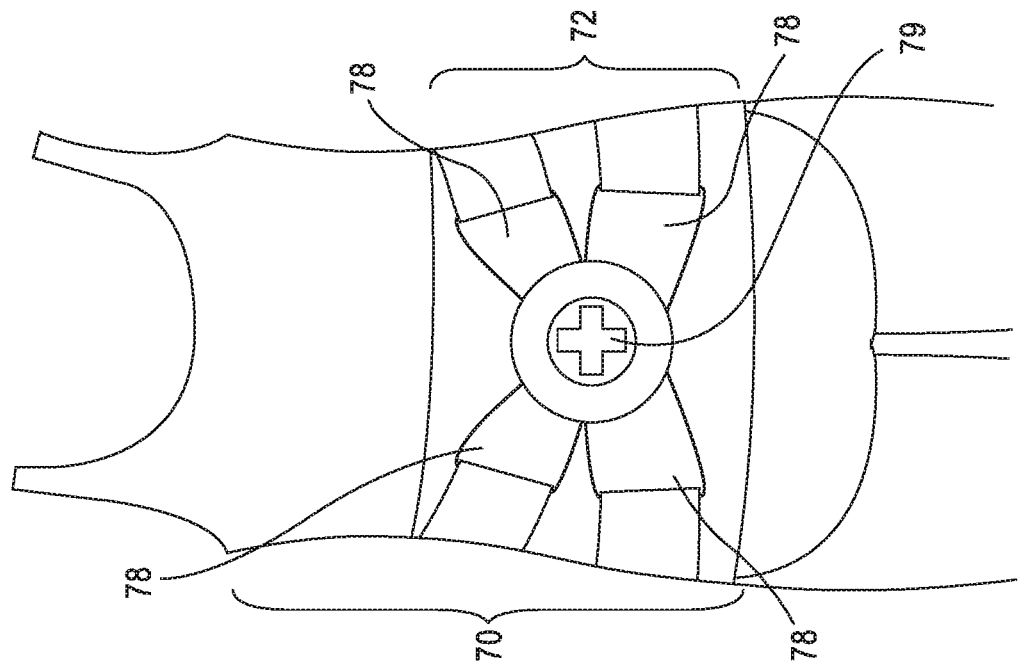
FIGS. 11A and 11B are a frontal and back perspective view of a female patient wearing an example apparatus in accordance with aspects of the present invention comprising an undergarment camisole that extends from the shoulders to the pubic line.
Figure 11A:
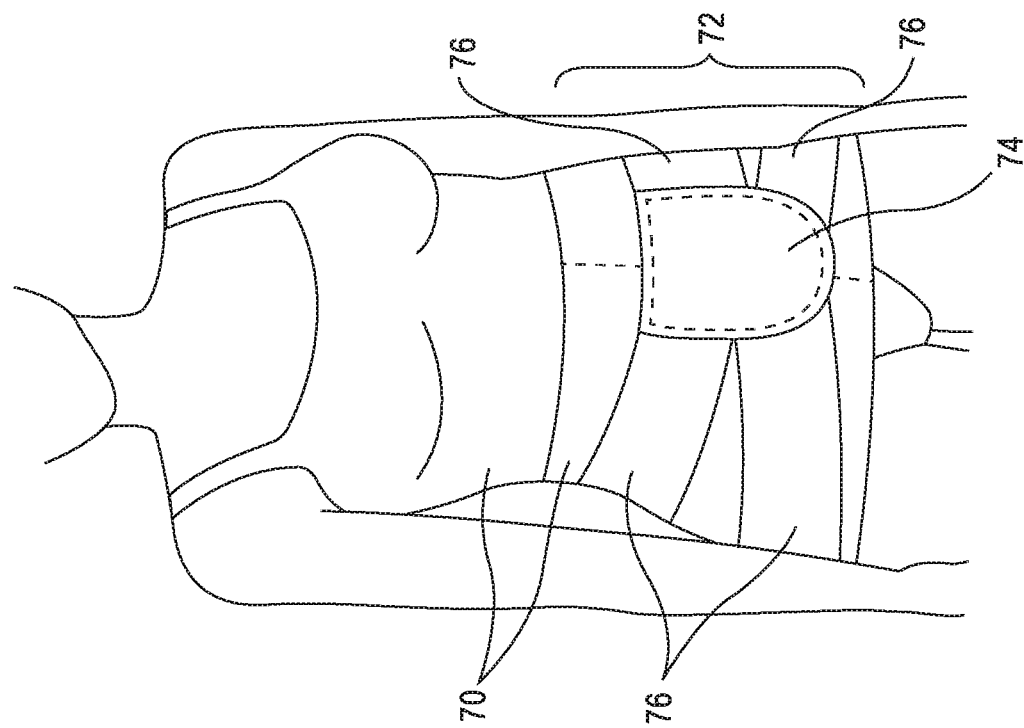

FIGS. 11A and 11B depict another example for female patients, comprising an undergarment camisole 70 with a butterfly compression mechanism 72 and an insert pouch 74. The camisole 70 extends from the patients shoulders across the torso and abdomen down to the pubic line. The camisole comprises a base material 50. Situated over the patient's lower abdomen, over top of the base material 50, is a butterfly compression mechanism 72 that features four straps 76 that originate from an oval shaped pouch 74, situated over the sigmoid colon to the left of the vertical midline of the abdomen. The pouch 74 is capable of holding various types of inserts including hot and cold packs, electro-stimulators, and biosensors. Each of the four straps 76 may be connected to a mechanism for adjusting the tension on the straps. For example, on the back side of the garment the straps may connect to a thin wire loop 78 that feed into a small circular crank situated in the middle of the patients back 79. This crank 79 allows the patient to easily adjust how intensely the pouch is compressed into the sigmoid colon. The pouch may be excluded, and the number of straps may be varied. For example, the apparatus may include only 2 straps instead of four. Instead, the two straps may be sewn along a vertical edge of the strap to the base material 50, directly above the sigmoid colon. Hook fabric may be sewn onto the end of each strap not sewn to the base material. The straps may then be stretched and wrapped around the patient's left and right hips, respectively, and attach to hook material on the back of the garment. This provides a simple way to provide compression to the sigmoid and descending colon, and to the abdomen generally, and may be desirable because the closing mechanism is on the back, where it will be less likely to be noticed.

Figure 12:
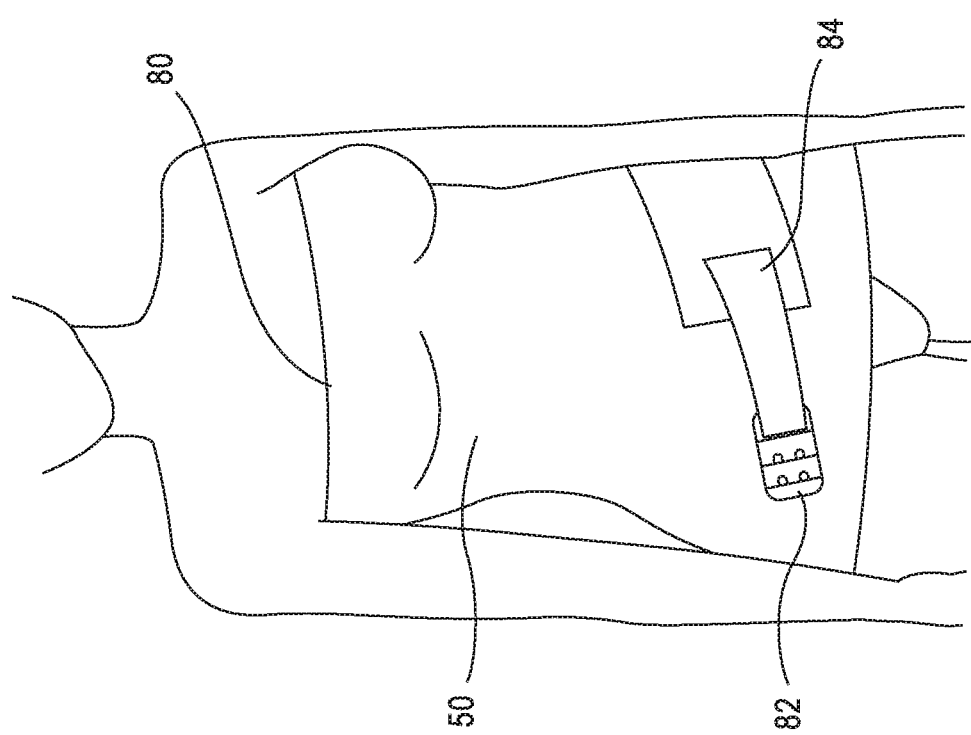
FIG. 12 is a frontal perspective view of a female patient wearing an example apparatus in accordance with aspects of the present invention comprising an undergarment tube top shirt that covers the breasts and torso and extends down to the pubic line.

FIG. 12 is another example for female patients. Aspects may include base materials 50 that extend from the pubic line to just above the breasts. For example, this may form a tube top type shirt or undergarment 80. Notable in this example is that the closing mechanism 82 for the adjustable sigmoid and descending colon compression strap mechanism 84 may comprise small, flexible plastic rings or clasps similar to those on a bra sewn into the base material 50 that the strap 84 can fasten onto at varying degrees of tension similar to a bra strap. This example offers sigmoid compression that is easily adjusted, yet is an alternative to the loop strips sewn onto the base material in a similar area as depicted in FIGS. 9A-9C.

Figure 13:
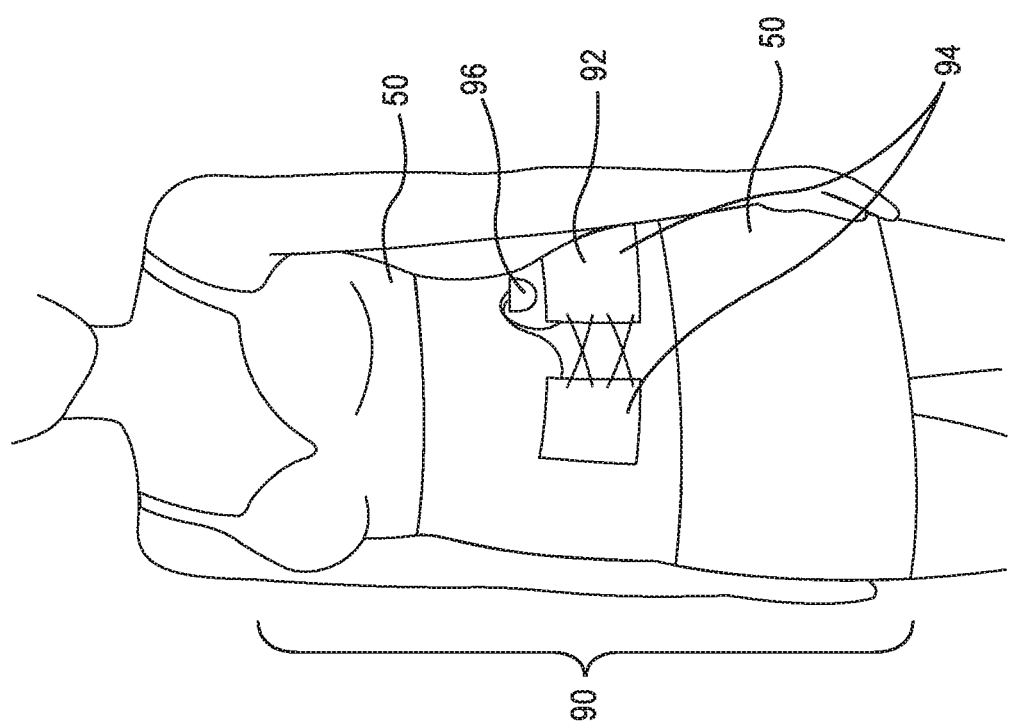
FIG. 13 is a frontal perspective view of a female patient wearing an example apparatus in accordance with aspects of the present invention comprising a body undergarment that covers the thighs, torso, and breasts, and has shoulder straps.

FIG. 13 illustrates an example in accordance with aspects of the present invention for females designed to be worn under formal clothing. The undergarment 90 may provide support for the bust, and extend down across the torso and pubic area all the way to the mid-thighs. The garment 90 may be divided into three horizontal sections, the top and bottom sections being comprising base material 50 and the middle section 94 comprising a knit fabric that may be selected to be slightly more firm and less elastic than the base material 50. Because this example 90 is designed to be worn under formal attire, it may be critical that its compression mechanism not be bulky or visible under a flat dress. Accordingly, a simple sigmoid compression mechanism is incorporated into this example, comprising 2 semi-elastic straps 94 sewn so that they lay horizontally in the middle section 92, and that when they lay flat, there is gap between the two straps 94 that falls overtop the sigmoid colon. The straps 94 are then pulled together by a simple string cinch 96 to generate compression. The excess string on the top of the cinch 96 can then be tucked into a small pocket.

Figure 14B:
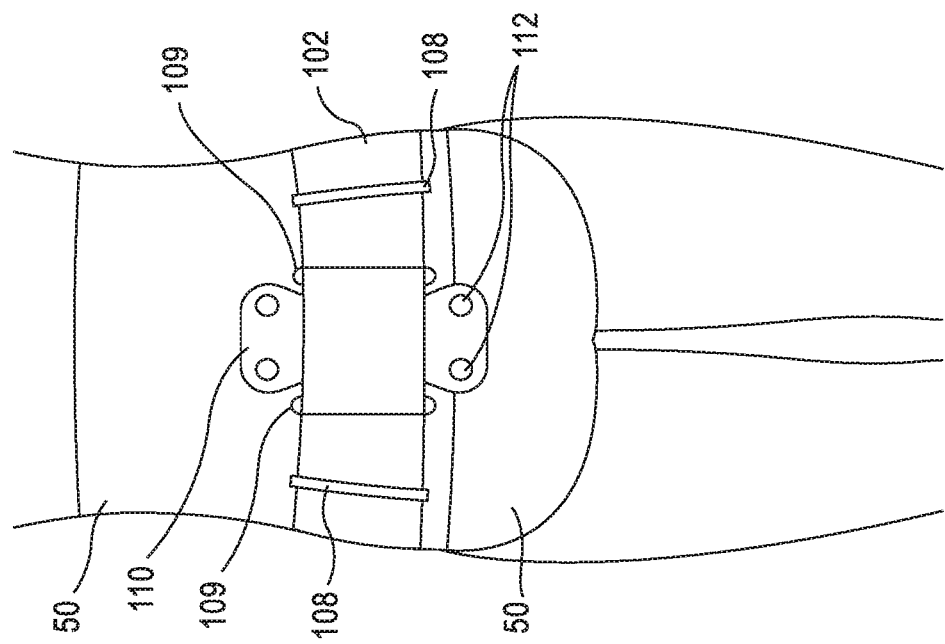
FIGS. 14A and 14B provide perspective views from the front and back of a female patient wearing an example apparatus in accordance with aspects of the present invention comprising underwear with a high rise torso cover that extends to the diaphragm.
Figure 14A:
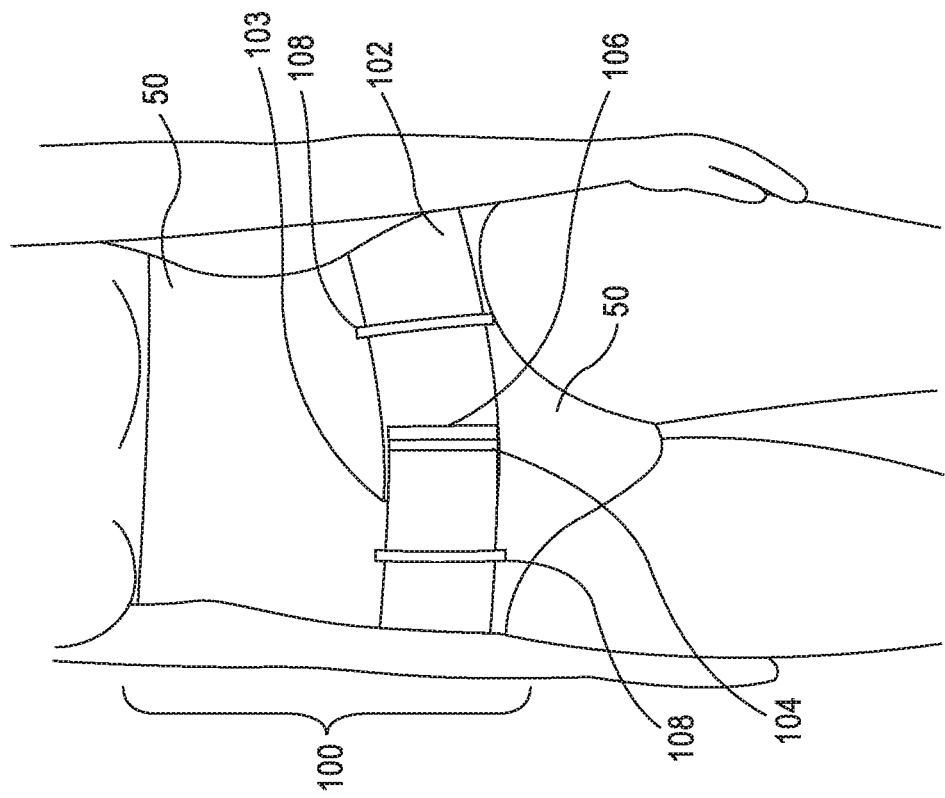

The example 100 depicted in FIGS. 14A and 14B includes an underwear undergarment for female patients that extends upward close the diaphragm, covering the torso. The garment 100 comprises a base material 50 and features an abdominal strap 102 that sits atop the base material 50 layer and circumvents the patient's lower abdomen. The strap 102 originates from and is sewn along its left vertical edge 103 to the base material 50 midway between the patient's umbilicus and right hip. The strap 102 circumvents the lower abdomen in a counter-clockwise loop, and is held in place by several loops 108 sewn to the base material 50 through which the strap 102 passes through. Once the strap 102 reemerges on the patient's right side, it may be pulled using the handle 104 and fastened securely using the closing mechanism 106 to the exterior side of the first part of the strap 102. Once tightly secured, the strap 102 will provide compression to the sigmoid and descending colon, as well as provide general abdominal wall resistance. On the patient's back, the strap passes through two loops in the base material 50 and overtop of a small lumbar massage tool 110. The lumbar massage tool 110 may include several semi-firm pressure nodes 112 that apply point-specific pressure to the lumbar muscles when the strap 102 is tightened. This may reduce bloating by relaxing the muscles in the lumbar area in order to provoke contraction of the abdominal wall musculature through the process of reciprocal inhibition.

Figure 15B:
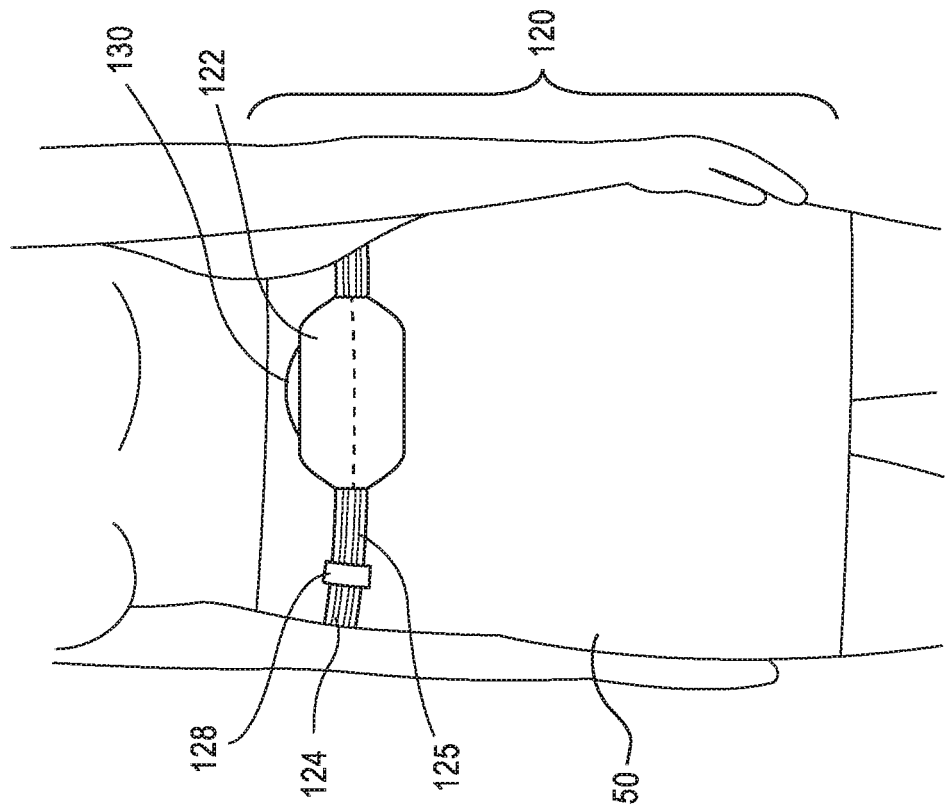
FIGS. 15A and 15B provide perspective views from the front and back of a female patient wearing an example apparatus in accordance with aspects of the present invention comprising hip and lower abdomen undergarment that extends from the mid-thighs up to just past the navel and umbilical line.
Figure 15A:
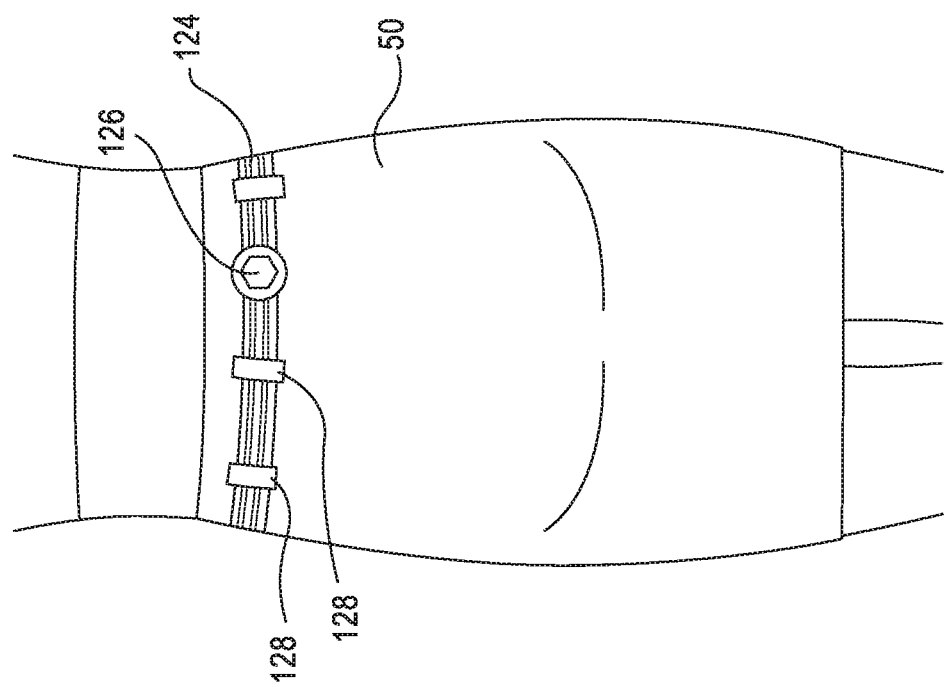

FIGS. 15A and 15B depict alternative example aspects 120 for females including an undergarment comprised of base material 50 that is worn about the hips and lower abdomen, extending from the mid-thigh up to a line a few inches past the umbilicus. A small pouch 122 may be situated upon the base material 50 over the sigmoid colon on the patient's front left side. The pouch is attached on either side to a band 124 that contains two small wires 125 that fit into thin channels in the band 124 that run along its length. Beginning on either side of the pouch 122 the bands 124 circumvent the patient's body and arrive at a closing mechanism 126 situated approximately behind the patient's right hip. The wires 125 extend upwards from the channels in the band into the closing mechanism 126. The patient can adjust the level of compression applied by the pouch 122 by turning the closing mechanism 126 clockwise or counter-clockwise. Situated in the pouch 122 is a removable insert 130 that is compressed into the sigmoid and descending colon when pressure is applied. The insert 130 may be comprised of an inert, semi-rigid or flexible shape, or a pneumatic, inflatable bladder that provides focused compression to the sigmoid or descending colon; it may be an insert that delivers hot, cold, or TENS therapy; it may be a patch or device capable of transdermal drug delivery, it also may be a biosensor or series of biosensors that measure physiological activity. The insert also may be equipped with wireless transmitting capabilities including Blue Tooth in order to transmit captured data to display devices (including computers, phones, tablets, etc.)

Figure 16:
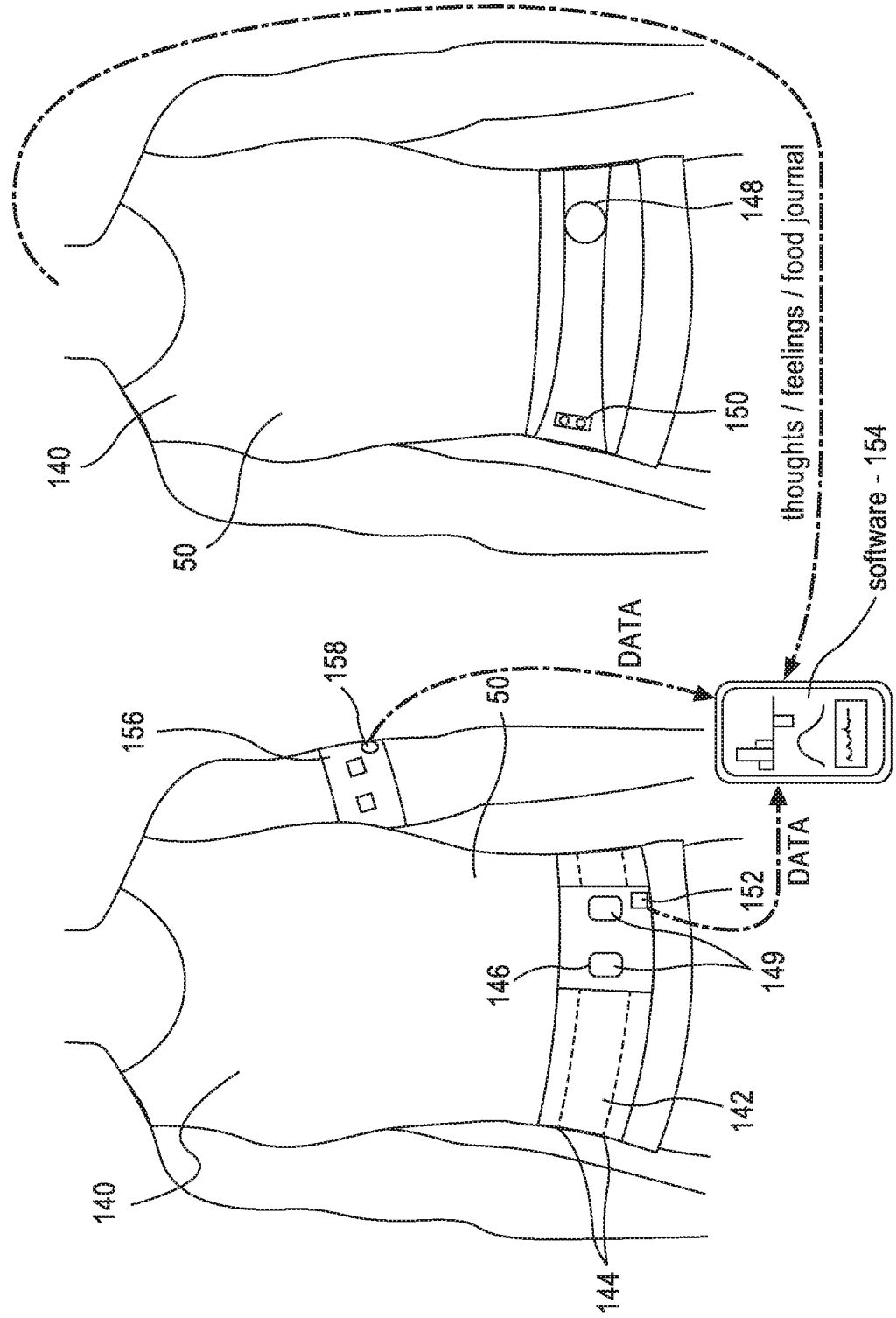
FIG. 16 provides perspective views from the front and back of a male patient wearing an example apparatus in accordance with aspects of the present invention comprising a sleeveless undergarment t-shirt that extends from the shoulders down across the torso to the pubic line.

FIG. 16 illustrates example aspects for males patients comprised of a sleeveless undergarment shirt 140 comprising base material 50 that extends from the shoulders to the pubic line. A small band 142 is sewn overtop of the base material 50 in a ring that is passes over the sigmoid and descending colon and circumvents the patients lower abdomen. There are two wires 144 embedded in the band that attach to the right and left side of an inelastic portion of the band 146 positioned over the sigmoid colon, and attach to a tightening mechanism 148 situated behind the patient's right hip. The base material 50 under the inelastic portion of the band 146 such that the inelastic portion 146 touches the patient's skin directly. Embedded in the inelastic portion 146 are several biosensors 149 that measure contractions in the lower bowel. These sensors 149 are powered by a small power source 150 embedded in the band 146 behind the patient's right hip. Also embedded into the inelastic portion of the band 146 may be a wireless transmitting mechanism 152 capable of storing and sending captured data to software 154 on a display device (such as a computer, mobile phone, or tablet). Another aspect may include a small band 156 not connected to the undergarment shirt 140 that the patient wears on their arm or leg. Embedded in the small band 156 may be several galvanic skin response sensors that measure electrical conductance of the skin. Skin conductance varies greatly based upon sweat-induced moisture. Sweating is controlled by the sympathetic nervous system, and thus skin conductance can be used as an indication of psychological (and physiological) arousal, including anxiety. The small band 156 could also be equipped with a wireless transmitting mechanism capable of storing and transmitting captured data to the software 154 on a display device. In conjunction, the software 154 could be able to display and analyze patterns and correlations between each data set to identify relationships between psychological arousal and dysmotility. The software 154 may also have a feature that would allow patients to input thoughts, feelings, and records of meals, and store and later combined this information with the relevant physiological data captured at that point in time.

Figure 17B:
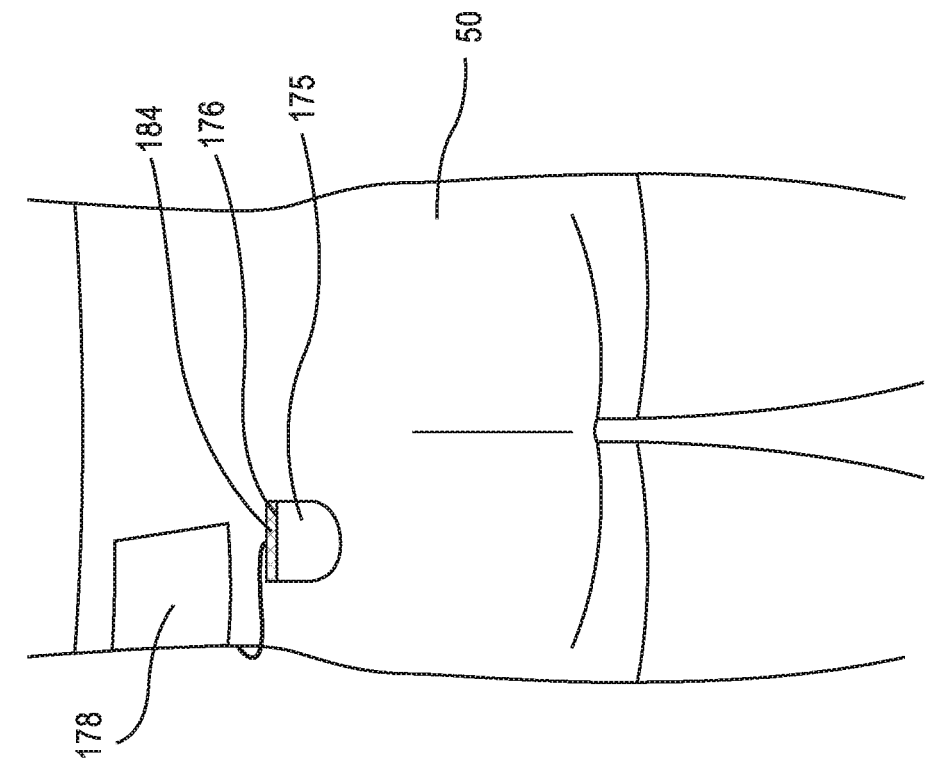
FIGS. 17A and 17B provide perspective views from the front and back of a male patient wearing an example apparatus in accordance with aspects of the present invention comprising underwear with a high rise cover that extends up just past the umbilical line.
Figure 17A:
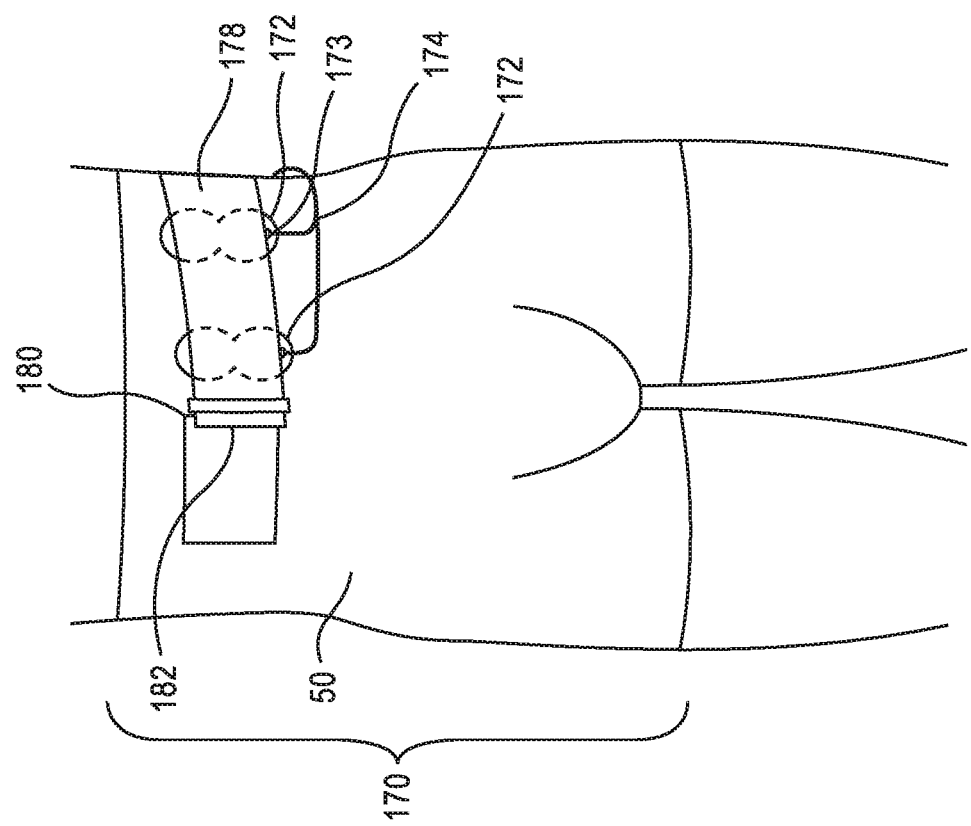

FIGS. 17A and 17B depict an example 170 having alternate aspects for male patients including boxer-briefs composed of base material 50 that extend from the upper thigh to a line slightly above the umbilicus. On the front side of the garment 170 in the area of the garment positioned over the patient's left lower abdomen, several transducers 172 are sewn on the inside of the base layer 50 such that the transducers 172 come into direct contact with the patient's skin. At the bottom of each transducer 172, there will be small ports that extend through the base layer 50 and that connect each transducer 172 to the wires 174 that connect to the power source 176. The power source 176 is contained in a small pouch 175 affixed to the external side of the base layer 50 on the patient's back. Furthermore there is a strap 178 with a handle 180 that applies compression to the sigmoid and descending colon over top of the transducers 172. Compression generated by the strap 178 may be adjusted using the closing mechanism 182. Electro-stimulation may be controlled and adjusted by the patient using controls built into the power source 176 or through another device (such as a mobile phone) that wirelessly communicates with the 176 power source using a wireless transmitting and receiving module 184 embedded in the power source 176.

Figure 18:
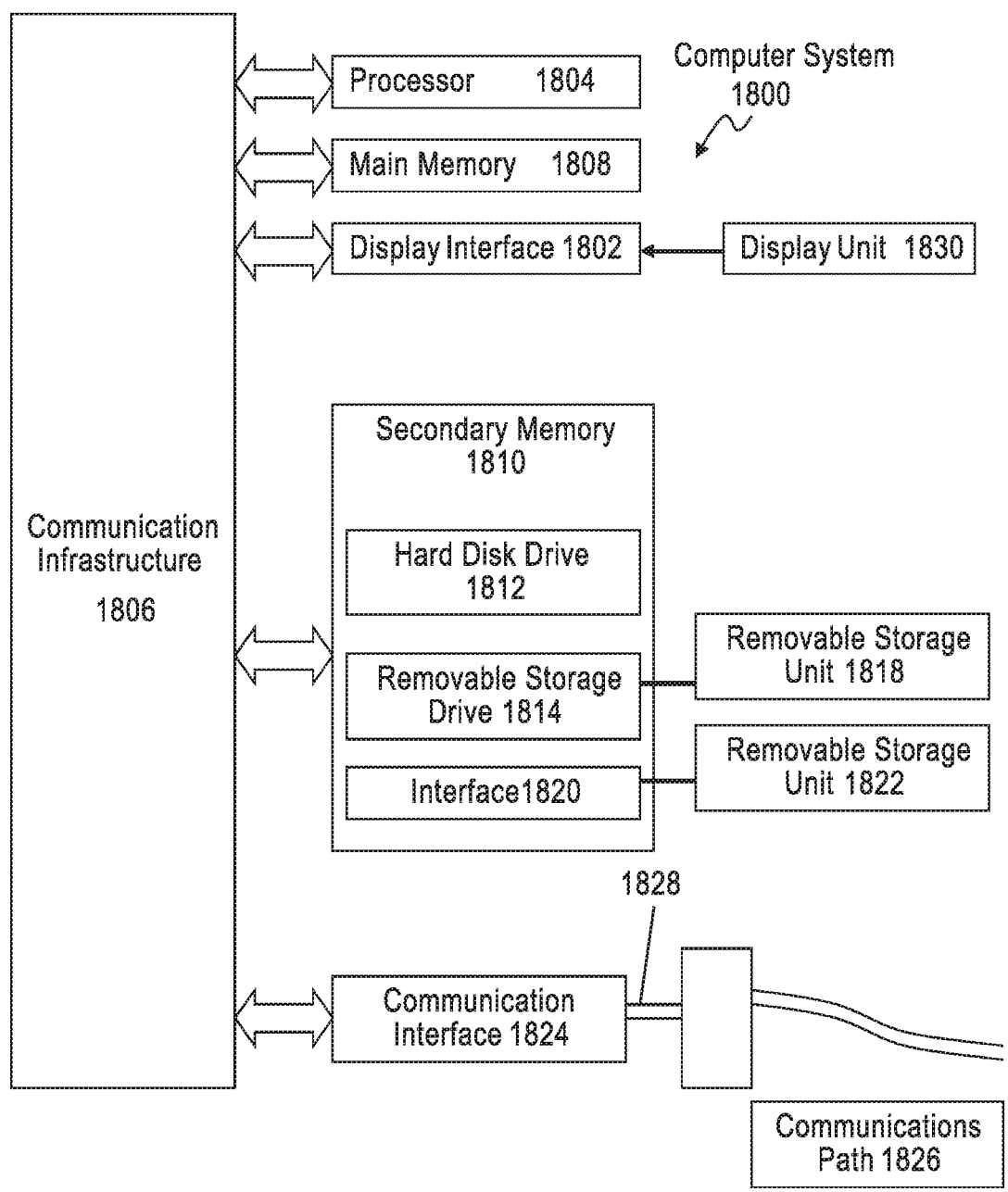
FIG. 18 presents an example system diagram of various hardware components and other features, for use in accordance with aspects of the present invention.

FIG. 18 presents an example system diagram of various hardware components and other features, for use in accordance with aspects presented herein. For example, among other aspects those including any of inserts within pouch 74, insert 130, wireless transmitting mechanism 152, software 154, wireless transmitting and receiving module 184 may be implemented using hardware, software, or a combination thereof and may be implemented in one or more computer systems or other processing systems. In one example, the aspects may include one or more computer systems capable of carrying out the functionality described herein. An example of such a computer system 1800 is shown in FIG. 18.

Computer system 1800 includes one or more processors, such as processor 1804. The processor 1804 is connected to a communication infrastructure 1806 (e.g., a communications bus, cross-over bar, or network). Various software aspects are described in terms of this example computer system. After reading this description, it will become apparent to a person skilled in the relevant art(s) how to implement the aspects presented herein using other computer systems and/or architectures.

Computer system 1800 can include a display interface 1802 that forwards graphics, text, and other data from the communication infrastructure 1806 (or from a frame buffer not shown) for display on a display unit 1830. Computer system 1800 also includes a main memory 1808, preferably random access memory (RAM), and may also include a secondary memory 1810. The secondary memory 1810 may include, for example, a hard disk drive 1812 and/or a removable storage drive 1814, representing a floppy disk drive, a magnetic tape drive, an optical disk drive, etc. The removable storage drive 1814 reads from and/or writes to a removable storage unit 1818 in a well-known manner. Removable storage unit 1818, represents a floppy disk, magnetic tape, optical disk, etc., which is read by and written to removable storage drive 1814. As will be appreciated, the removable storage unit 1818 includes a computer usable storage medium having stored therein computer software and/or data.

In alternative aspects, secondary memory 1810 may include other similar devices for allowing computer programs or other instructions to be loaded into computer system 1800. Such devices may include, for example, a removable storage unit 1822 and an interface 1820. Examples of such may include a program cartridge and cartridge interface (such as that found in video game devices), a removable memory chip (such as an erasable programmable read only memory (EPROM), or programmable read only memory (PROM)) and associated socket, and other removable storage units 1822 and interfaces 1820, which allow software and data to be transferred from the removable storage unit 1822 to computer system 1800.

Computer system 1800 may also include a communications interface 1824. Communications interface 1824 allows software and data to be transferred between computer system 1800 and external devices. Examples of communications interface 1824 may include a modem, a network interface (such as an Ethernet card), a communications port, a Personal Computer Memory Card International Association (PCMCIA) slot and card, etc. Software and data transferred via communications interface 1824 are in the form of signals 1828, which may be electronic, electromagnetic, optical or other signals capable of being received by communications interface 1824. These signals 1828 are provided to communications interface 1824 via a communications path (e.g., channel) 1826. This path 1826 carries signals 1828 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 980, a hard disk installed in hard disk drive 970, and signals 1828. These computer program products provide software to the computer system 1800. Aspects presented herein may include such computer program products.

Computer programs (also referred to as computer control logic) are stored in main memory 1808 and/or secondary memory 1810. Computer programs may also be received via communications interface 1824. Such computer programs, when executed, enable the computer system 1800 to perform the features presented herein, as discussed herein. In particular, the computer programs, when executed, enable the processor 1810 to perform the features presented herein. Accordingly, such computer programs represent controllers of the computer system 1800.

In aspects implemented using software, the software may be stored in a computer program product and loaded into computer system 1800 using removable storage drive 1814, hard drive 1812, or communications interface 1820. The control logic (software), when executed by the processor 1804, causes the processor 1804 to perform the functions as described herein. In another example, aspects may be implemented primarily in hardware using, for example, hardware components, such as application specific integrated circuits (ASICs). Implementation of the hardware state machine so as to perform the functions described herein will be apparent to persons skilled in the relevant art(s).

In yet another example, aspects presented herein may be implemented using a combination of both hardware and software.

Figure 19:
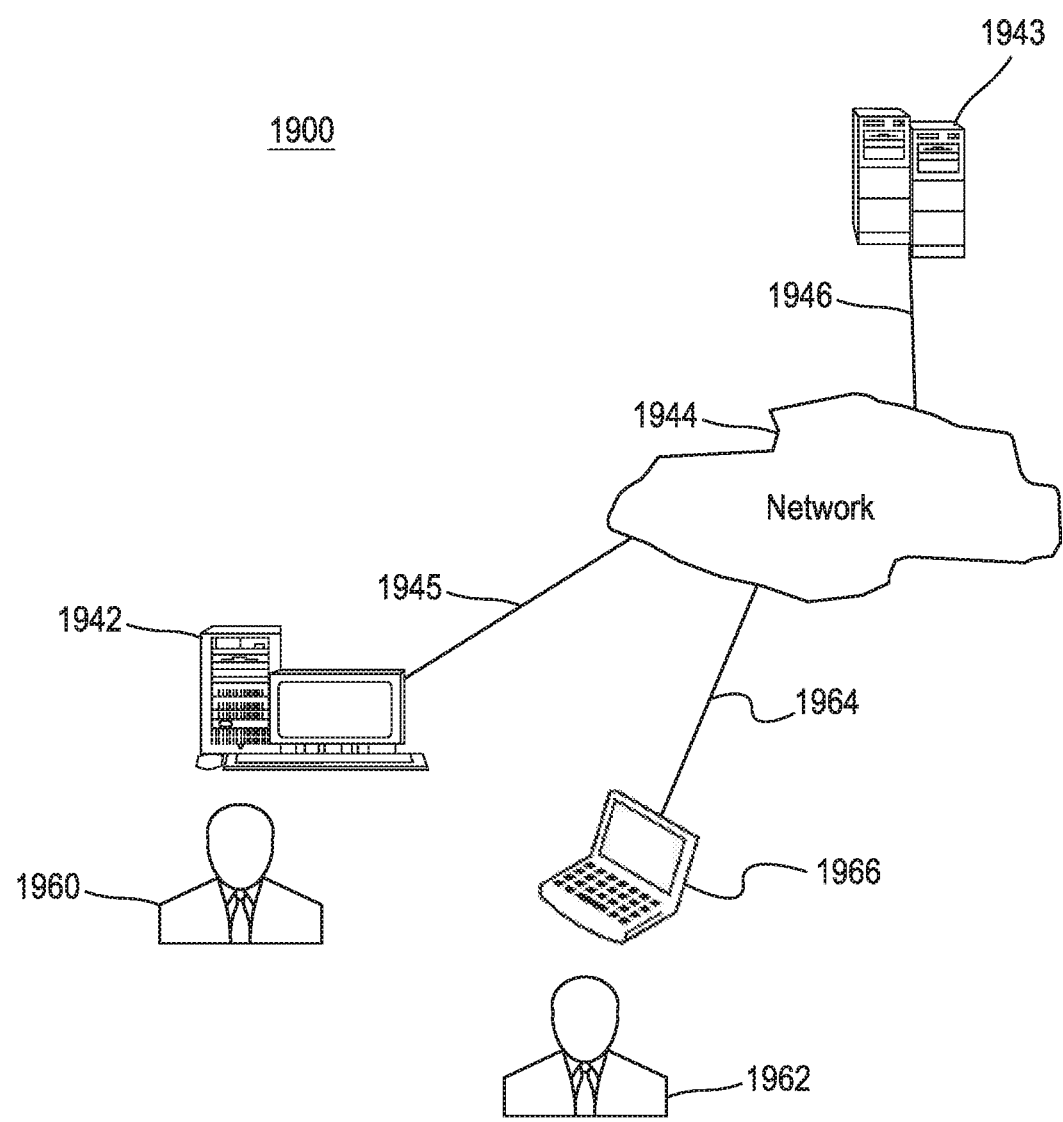
FIG. 19 is a block diagram of various example computer system components, in accordance with aspects of the present invention.

FIG. 19 is a block diagram of various example system components, in accordance with aspects presented herein. FIG. 19 shows a communication system 1900 usable in accordance with the present invention. The communication system 1900 includes one or more accessors 1960, 1962 (also referred to interchangeably herein as one or more "users") and one or more terminals 1942, 1966. In one aspect, data for use in accordance aspects presented herein, for example, input and/or accessed by accessors 1960, 1964 via terminals 1942, 1966, such as personal computers (PCs), minicomputers, mainframe computers, microcomputers, telephonic devices, or wireless devices, such as personal digital assistants ("PDAs") or a hand-held wireless devices coupled to a server 1943, such as a PC, minicomputer, mainframe computer, microcomputer, or other device having a processor and a repository for data and/or connection to a repository for data, via, for example, a network 1944, such as the Internet or an intranet, and couplings 1945, 1946, 1964. The couplings 1945, 1946, 1964 include, for example, wired, wireless, or fiberoptic links. In another aspect, the method and system presented herein operate in a stand-alone environment, such as on a single terminal.

Figure 20:
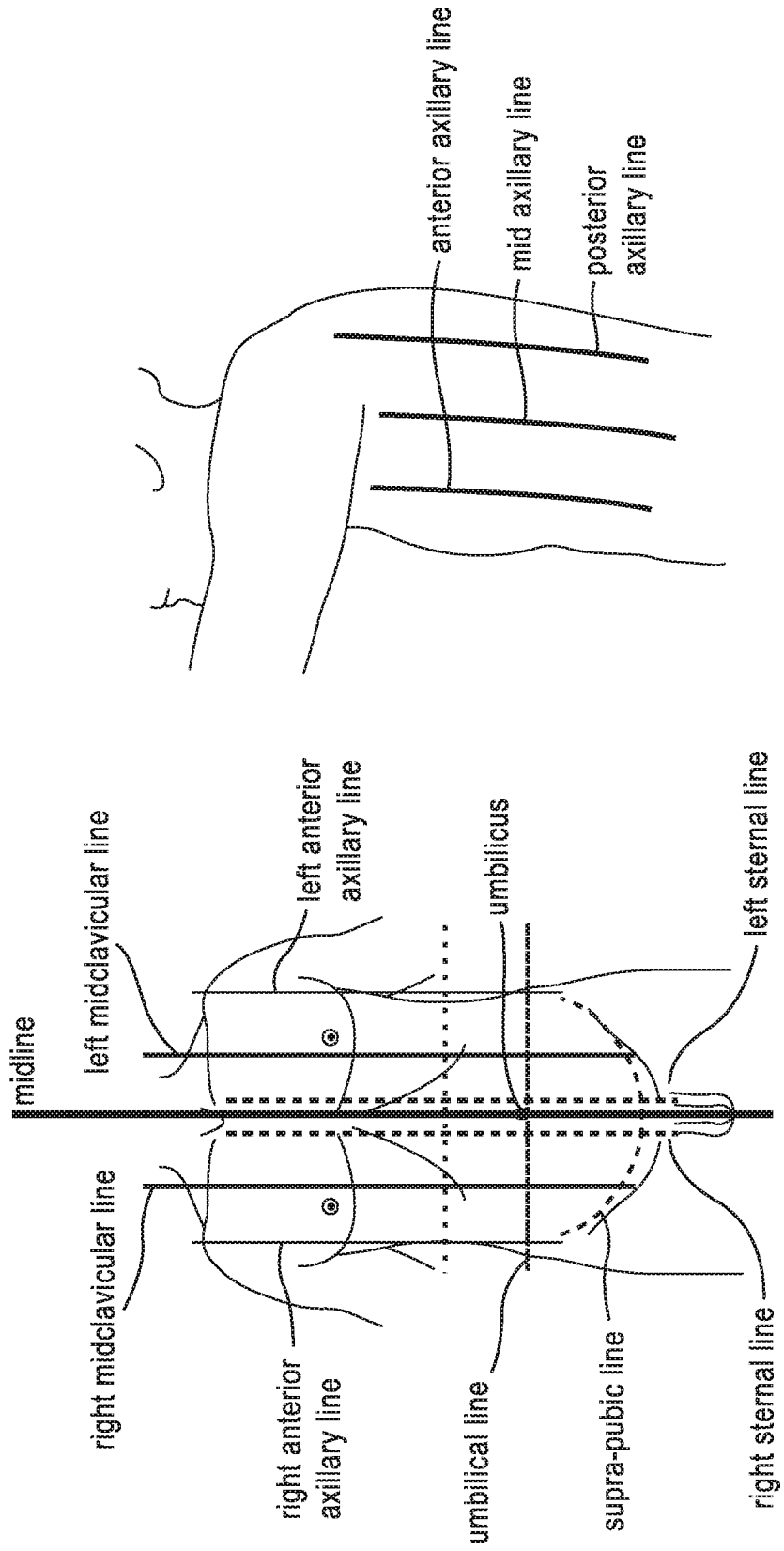
FIGS. 20A and 20B are diagrams that depict anatomical references used to describe areas and planes across the front and side of the human torso.
Figure 21:
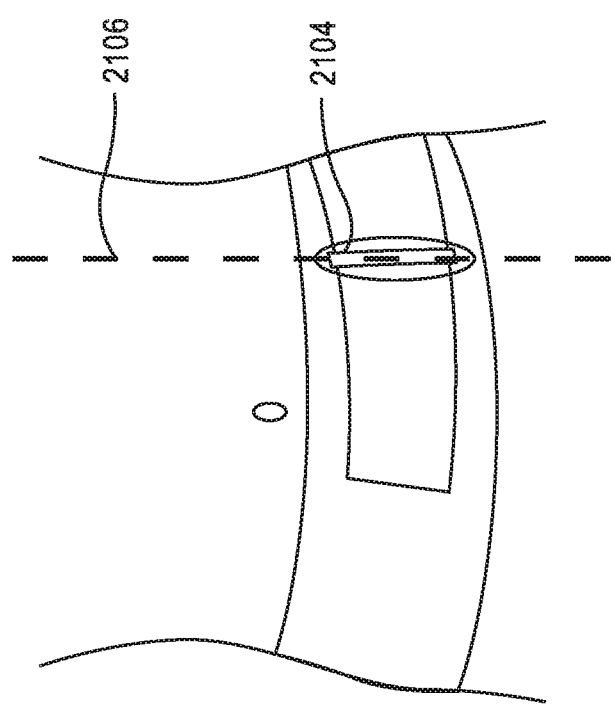
FIG. 21 is a frontal perspective of the lower abdomen of a patient wearing an example apparatus in accordance with aspects of the present invention comprising an abdominal band.

As depicted in FIG. 21, other aspects of the present invention may include an elastic or semi-elastic band 40 or garment base material 50 that is fastened around the abdomen and has one or more secondary bands, with each secondary band attached to the primary band 40 or base material 50 along one vertical edge 2104 that is coincident with the left midclavicular line 2106, as depicted in FIG. 20A, when the band is fastened around the abdomen or the garment is worn.

Figure 22:
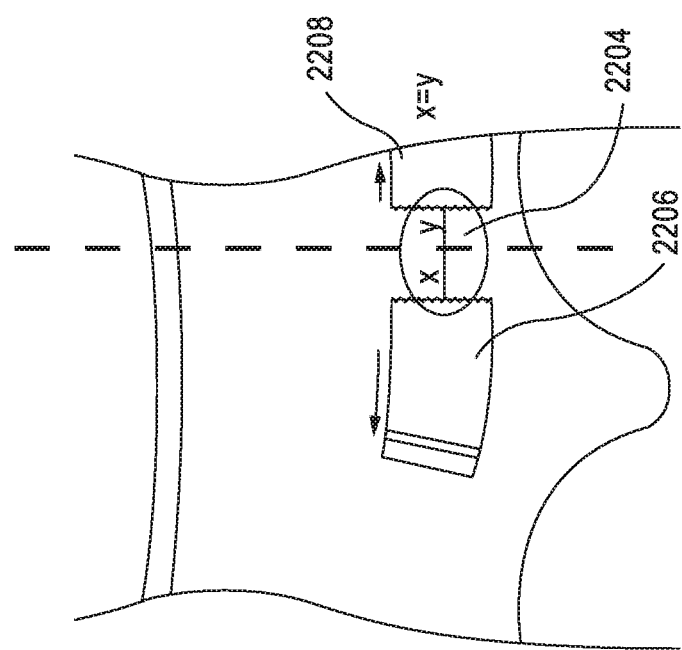
FIG. 22 is a frontal perspective of the lower abdomen of a patient with the left midclavicular line indicated, wearing an example apparatus in accordance with aspects of the present invention comprising an underwear bottom with an undergarment extension that covers the torso up to the rib line.

FIG. 22 depicts a similar secondary band configuration, except that the secondary bands are not attached to the band 40 or garment 50 along the same vertical line, coincident with the left midclavicular line, but are instead attached along vertical lines equidistance 2204 from left midclavicular line. In this aspect, the secondary band attached to the right of the left midclavicular line (from the perspective of the wearer) 2206 is configured to stretch horizontally (longitudinally) from left to right, and the secondary band attached to the left of the left midclavicular line 2208 is configured to stretch from horizontally (longitudinally) from right to left. It is important to note that aspects of this invention allow various combinations of base materials, garment styles (such as abdominal bands and shape-fitting undergarments), closing mechanisms, and compression mechanisms to suit the preference of the user. For example, in FIG. 22 the secondary band configuration is incorporated into a female underwear undergarment that extends up across the torso to just below the bust line, a style similar to the aspect depicted in FIG. 10.

In aspects of the invention incorporating one or more adjustable secondary straps that generate compression when stretched and fastened, it may be advisable that the straps are designed in such a way so that the full, intended treatment range of compression can be achieved through adjustment by a user who is wearing the device at the time. Practically, if compression level is adjusted by stretching or relaxing the tension in one or more secondary bands and then (re)-fastening the secondary band(s) to the band or base material, then the apparatus and secondary bands must be capable of generating intended compression levels taking into account that the areas of the band or base material to which the secondary straps may be attached will be limited to the areas that the user can easily reach while wearing the device. FIGS. 23A and 23B depict areas of the band 40 to which the user's reach will limit where the secondary straps may be fastened. With respect to the secondary strap 2308 that stretches from left to right, the circumferential region of possible attachment 2304 is bound approximately by the anterior midline and the left posterior axillary line. Reciprocally, the secondary strap 2310 that stretches from right to left is bound by the left anterior axillary line and the posterior midline. In this aspect, the elasticity of the secondary bands must be of a level that allows for the intended treatment levels of compression to be achieved when the secondary bands are stretched and fastened to the band 40 within the respective zones (2304, 2306). Of note, no vertical bounds to the zones of possible secondary strap fastening are described. Although vertical bounds are apparent in FIG. 22, it is the style and application area of the band 40 or garment 50 that may vertically limit the area to which a user can fasten the secondary strap rather than the anatomical features of the wearer.

Figure 24:
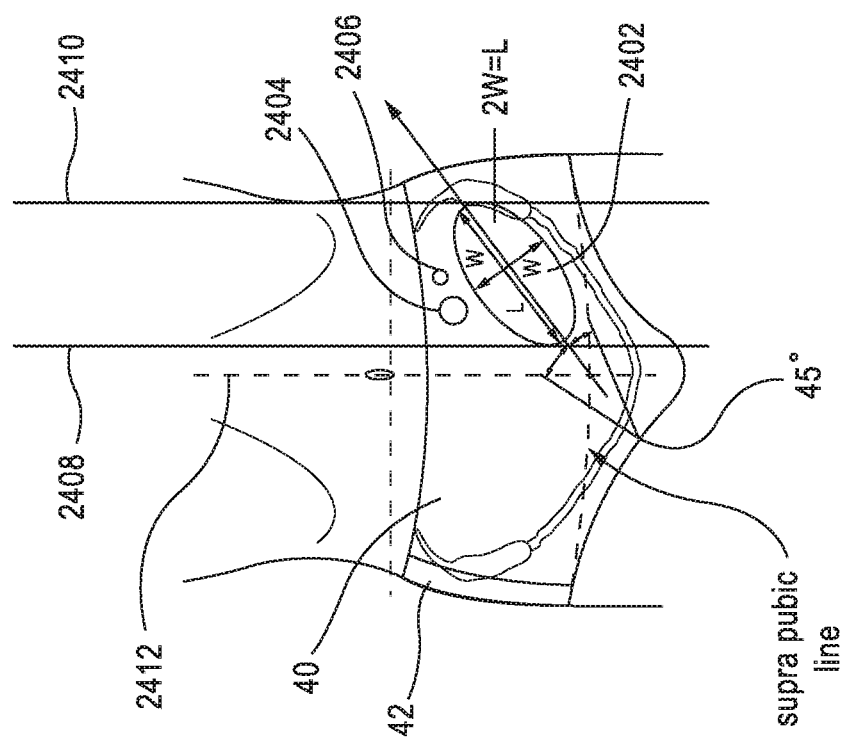
FIG. 24 provides a perspective view from the front of a female patient with the suprapubic line indicated, wearing an example apparatus in accordance with aspects of the present invention comprising underwear that extends up to just below the umbilical line.

In alternative aspects of the invention, the band or garment base material may include a pad or an inflatable air bladder specifically designed to apply compression to the left lower abdomen and sigmoid colon. FIG. 24 depicts a band 40 with a closing mechanism 42 used to connect one end of the band to the other end of the band around a user's lower abdomen with an embedded air bladder 2402, air pump 2404, and pressure gauge 2406. In this aspect, the air bladder 2402 is positioned over the left lower abdomen when the band 40 is applied. The shape of the air bladder 2402 in this aspect is oblong, with a length approximately twice its width. The air bladder 2402 is oriented longwise at a 30-60 degree angle (from horizontal), with its right side lower than its left side. In FIG. 24 the angle depicted is 45 degrees. The air bladder 2402 may be positioned, attached, or embedded in the band 40 in a way that when the band is properly fastened, the air bladder 2402 is positioned within the left lower abdomen and approximately between the left sternal line 2408 and the left anterior axillary line 2410 (both lines are also depicted in FIGS. 20A and 20B)—although in other aspects, the position of the bladder may extend horizontally to or just past the midline 2412. Compression may be applied and adjusted by inflating and deflating the air bladder 2402 using the embedded air pump 2404.

Figure 25:
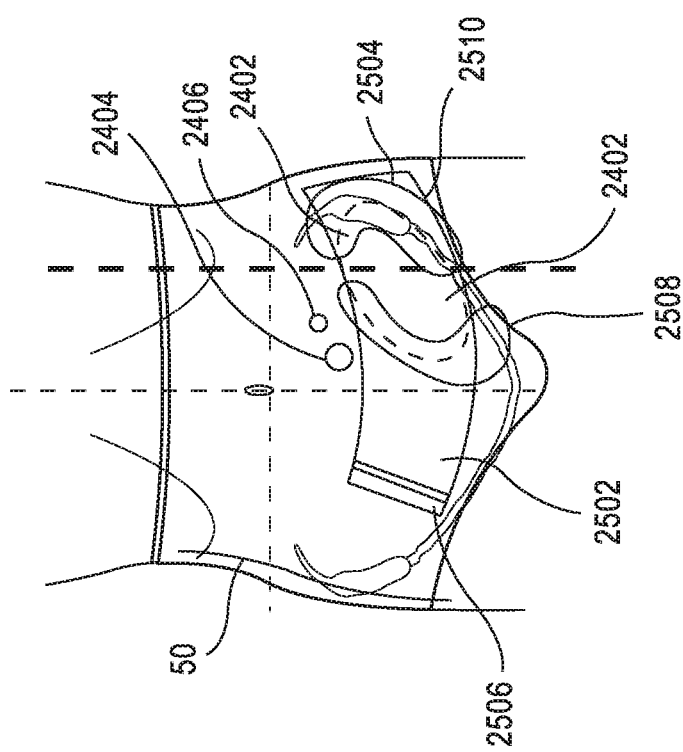
FIG. 25 provides a perspective view from the front of a female patient with the left midclavicular line indicated, wearing an example apparatus in accordance with aspects of the present invention comprising an underwear bottom with an undergarment extension that covers the torso up to the rib line.

FIG. 25 depicts a base material 50 with an embedded air bladder 2402, air pump 2404, and pressure gauge 2406, as well as two secondary straps 2502/2504, each with a closing mechanism 2506 allowing the straps 2502/2504 to be fastened to the exterior of the base material 50. In this aspect, the secondary straps 2502/2504 may be attached or sewn to the base material along their left (2502) and right (2504) edges in a way so that the line upon which each strap is sewn or attached to the base material is coincident with approximately one side of the contour of the air bladder. These lines of attachment are indicated in FIG. 25 as 2508 and 2510. The contoured attachment line may provide improved fit and comfort, and may maximize the efficiency of the force exerted by the secondary straps used to compress the air bladder into the left lower abdomen.

Figure 26:
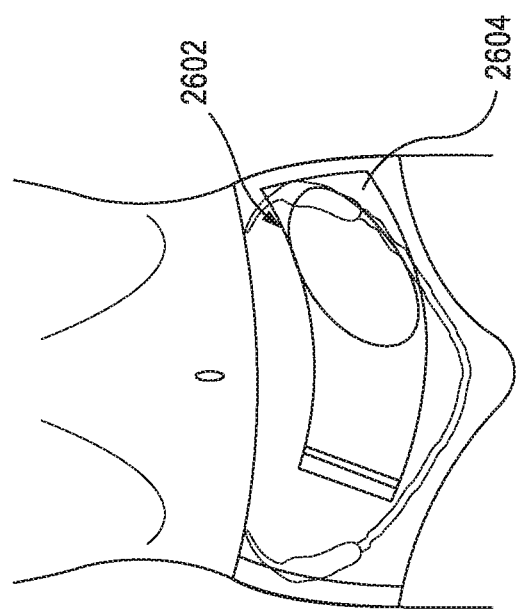
FIG. 26 provides a perspective view from the front of a female patient wearing an example apparatus in accordance with aspects of the present invention comprising an abdominal band.

FIG. 26 reflects an alternative aspect of the invention, and depicts a band with an embedded or inserted pad 2602, similarly shaped and positioned to the air bladder described in FIG. 24, with a secondary strap 2604 that stretches horizontally across the location of the pad so that when it is fastened to the exterior of the band, it compresses the pad 2602 into the left lower abdomen.

Thus, aspects may include an apparatus, system, or method for treating symptoms of IBS that provide patients with treatment that can be initiated and have a treatment level adjusted in real-time, in acute response to symptoms. This provides a patient with real time symptom management. For example, an apparatus may comprise an elastic portion capable of applying compression across the abdomen of a user and a component capable of applying adjustable compression to a target area in order to adjust treatment of IBS symptoms.

Aspects may further include a method or apparatus for treatment of dysmotility associated with IBS and/or other functional GI disorders. The method may include applying external compression to at least a sigmoid colon and/or lower left abdomen of a patient. Aspects may further include applying compression to a descending colon, e.g., in a left middle portion of the patient's abdomen in order to promote bowel relaxation and/or reduction of bowel spasms. Compression may be applied, maintained, and/or adjusted, e.g. using an apparatus as described herein.

Aspects may further include a method or apparatus for treating abdominal pain associated with IBS or other functional GI disorders. The method may include applying external compression to at least a sigmoid colon/left lower abdomen of a patient in a manner configured to block/dampen visceral pain signal transmission to the brain of the patient. The method may include applying compression to the descending colon (left middle abdomen) and the lower abdomen generally in order to block/dampen visceral pain signal transmission to the brain. Compression may be applied, maintained, and/or adjusted, e.g. using an apparatus as described herein.

Aspects may further include a method or apparatus for treating distention and bloating associated with IBS or other functional GI disorders. The method may comprise applying external compression to at least the sigmoid colon/left lower abdomen of a patient in a manner configured to prevent excessive expansion of the colon lumen due the accumulation of intestinal gas in that region of the colon. The method may further include applying compression to the descending colon (left middle abdomen) of the patient, in order to prevent excessive expansion of the colon lumen due the accumulation of intestinal gas in that region of the colon. Compression may be applied, maintained, and/or adjusted, e.g. using an apparatus as described herein.

Aspects may further include a method or apparatus for treating distention and bloating associated with IBS or other functional GI disorders. The method may include applying external compression across the abdominal wall of a patient as a means to oppose and resist relaxation of the abdominal wall that occurs in response to intestinal gas and pressure. Compression may be applied, maintained, and/or adjusted, e.g. using an apparatus as described herein.

Aspects may further include a method or apparatus for treating distention and bloating associated with IBS or other functional GI disorders. The method may comprise promoting relaxation of the muscles of the lower back and lumbar region through the use of wearable massage mechanisms in order to provoke reciprocal contraction of the abdominal wall in order to oppose and resist relaxation of the abdominal wall that occurs in response to intestinal gas and pressure. The apparatus may comprise an apparatus include aspects presented herein and may further include a massage mechanism configured to provide a massaging action to a lower back or lumbar region of a patient wearing the apparatus.

Aspects may further comprise a method or apparatus for treating distention and bloating associated with IBS or other functional GI disorders. The apparatus may comprise a wearable configured to detect abdominal wall contraction. The wearable may be configured to alert a user when unconscious abdominal wall relaxation is occurring so that the user may consciously contract their abdominal wall and oppose the relaxation and distention. The wearable may be configured to allow adjustment a compression applied to a lower abdomen of the user. For example, upon receiving the alert, the user may determine whether to adjust the compression. In another example, the wearable may automatically adjust a level of compression based on detecting abdominal wall relaxation. For example, when abdominal wall contraction is measured above a set level, the wearable may automatically adjust the compression. Compression may be applied, e.g., using aspects presented herein.

Example aspects of the present invention have now been described in accordance with the above advantages. It will be appreciated that these examples are merely illustrative of aspects of the present invention. Many variations and modifications will be apparent to those skilled in the art.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claim presents elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A system comprising:
   memory; and
   at least one processor coupled to the memory and configured to:
      receive a first set of data from one or more non-invasive biosensors configured to measure physiological data including contractions in a bowel of a user;
      determine a pattern associated with dysmotility based on the first set of data from the one or more non-invasive biosensors; and
      provide one or more stimulus from a non-invasive component to the bowel of the user in response to the pattern associated with the dysmotility based on the first set of data.

2. The system of claim 1, wherein the at least one processor is further configured to:
   receive a second set of data from a galvanic skin response sensor configured to measure electrical conductance of skin of the user; and
   analyze patterns between the first set of data and the second set of data.

3. The system of claim 2, further comprising the galvanic skin response sensor.

4. The system of claim 1, further comprising the one or more non-invasive biosensors.

5. The system of claim 4, further comprising an apparatus for treating symptoms of Irritable Bowel Syndrome (IBS), including:
   a base material comprising a material that fits to a body of the user;
   an elastic portion capable of applying compression across an abdomen of the user; and
   a portion comprising the one or more non-invasive biosensors.

6. The system of claim 5, wherein the apparatus further includes a tension adjusting mechanism for adjusting the compression applied to the abdomen in order to treat the symptoms of IBS.

7. The system of claim 1, wherein the first set of data received from the one or more non-invasive biosensors further includes at least one or heart rate, perspiration, or bowel movements.

8. The system of claim 1, wherein the one or more stimulus includes at least one of an electrical stimulus, a magnetic stimulus, or a sonic stimulus.

9. The system of claim 1, wherein the one or more stimulus is configured to induce muscle relaxation or muscle contraction in the bowel of the user.

10. The system of claim 1, wherein the at least one processor is further configured to provide biofeedback in response to receiving the first set of data.

11. The system of claim 1, wherein the at least one processor is further configured to wirelessly transmit information about the first set of data to a display device.

12. The system of claim 1, wherein the at least one processor is further configured to:
  generate an analyzed set of data based on the determined pattern.

13. The system of claim 12, wherein the at least one processor is further configured to:
  receive user input regarding at least one selected from a group consisting of thoughts, feelings, and records of meals; and
  correlate the user input to the analyzed set of data.

14. The system of claim 12, wherein the at least one processor is further configured to:
  receive user input of a record of one or more meals; and
  correlate the user input to the analyzed set of data.

15. The system of claim 1, wherein the one or more stimulus includes compression of the bowel of the user.

16. The system of claim 1, wherein the at least one processor is further configured to:
  detect an abdominal wall relaxation indicating bloating or distention based on second data from the one or more non-invasive biosensors; and
  provide an alert to the user in response to the abdominal wall relaxation.

17. The system of claim 16, wherein the at least one processor is further configured to perform, in response to the abdominal wall relaxation, at least one of:
  automatically adjust a level of compression in response to the abdominal wall relaxation,
  apply electrical stimulation to provoke muscle contraction in an abdomen, or
  apply a mechanical stimulation to provoke an abdominal reflex.

18. The system of claim 16, wherein the abdominal wall relaxation is detected based on an increase in abdominal circumference.

19. A method of measurement of bowel contraction data, comprising:
  receiving, via at least one processor, a first set of data from one or more non-invasive biosensors configured to measure physiological data including contractions in a bowel of a user;
  determining a pattern associated with dysmotility based on the first set of data from the one or more non-invasive biosensors; and
  providing one or more stimulus from a non-invasive component to the bowel of the user in response to the pattern associated with the dysmotility based on the first set of data.

20. The method of claim 19, further comprising:
  receiving a second set of data from a galvanic skin response sensor configured to measure electrical conductance of skin of the user; and
  identifying patterns between the first set of data and the second set of data.

21. The method of claim 19, wherein the first set of data received from the one or more non-invasive biosensors further includes at least one or heart rate, perspiration, or bowel movements.

22. The method of claim 19, wherein the one or more stimulus includes at least one of an electrical stimulus, a magnetic stimulus, or a sonic stimulus.

23. The method of claim 19, wherein the one or more stimulus is configured to induce muscle relaxation or muscle contraction in the bowel of the user.

24. The method of claim 19, further comprising:
  providing biofeedback in response to receiving the first set of data.

25. The method of claim 19, further comprising:
  wirelessly transmitting information about the first set of data to a display device.

26. The method of claim 19, further comprising:
  generating an analyzed set of data based on the determined pattern.

27. The method of claim 26, further comprising:
  receiving user input regarding at least one selected from a group consisting of thoughts, feelings, and records of meals; and
  correlating the user input to the analyzed set of data.

28. The method of claim 26, further comprising:
  receiving user input of a record of one or more meals; and
  correlating the user input to the analyzed set of data.

29. The method of claim 19, wherein the one or more stimulus includes artificial abdominal wall resistance for the bowel of the user.

30. The method of claim 19, further comprising:
  detecting an abdominal wall relaxation indicating bloating or distention based on second data from the one or more non-invasive biosensors; and
  providing an alert to the user in response to the abdominal wall relaxation.

31. The method of claim 30, further comprising performing, in response to detection of the abdominal wall relaxation, at least one of:
  automatically adjusting a level of compression in response to the abdominal wall relaxation,
  applying electrical stimulation to provoke muscle contraction in an abdomen, or
  apply a mechanical stimulation to provoke an abdominal reflex.

32. The method of claim 30, wherein the abdominal wall relaxation is detected based on an increase in abdominal circumference.

* * * * *